US010881859B2

(12) United States Patent
Brill et al.

(10) Patent No.: US 10,881,859 B2
(45) Date of Patent: Jan. 5, 2021

(54) STEERING OF TARGET POLES IN AN ELECTRODE ARRAY IN A PULSE GENERATOR SYSTEM

(71) Applicant: Boston Scientific Neuromodulation Corporation, Valencia, CA (US)

(72) Inventors: Natalie A. Brill, Sherman Oaks, CA (US); Yue Li, Encino, CA (US); Jun Park, La Crescenta, CA (US); Dheerendra Kashyap, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 96 days.

(21) Appl. No.: 16/210,794

(22) Filed: Dec. 5, 2018

(65) Prior Publication Data

US 2019/0175915 A1    Jun. 13, 2019

Related U.S. Application Data

(60) Provisional application No. 62/598,114, filed on Dec. 13, 2017.

(51) Int. Cl.
*A61N 1/36* (2006.01)
*A61N 1/372* (2006.01)
(Continued)

(52) U.S. Cl.
CPC ....... *A61N 1/36185* (2013.01); *A61N 1/0476* (2013.01); *A61N 1/0553* (2013.01); *A61N 1/36157* (2013.01); *A61N 1/37247* (2013.01)

(58) Field of Classification Search
None
See application file for complete search history.

(56) References Cited

U.S. PATENT DOCUMENTS 6,516,227 B1   2/2003  Meadows et al.
8,412,345 B2 * 4/2013  Moffitt .................. G16H 20/30
                                                    607/67
(Continued)

FOREIGN PATENT DOCUMENTS

EP       2709721      9/2016
WO    2006/029090    3/2006

OTHER PUBLICATIONS

Precision Spectra™ System Programming Manual, Boston Scientific Corp., 90834018-18 Rev A (2016).E. Viezi et al., "Spinal Cord Stimulation (SCS) with Anatomically Guided (3D) Neural Targeting Shows Superior Chronic Axial Low Back Pain Relief Compared to Traditional SCS—LUMINA Study," Pain Medicine, pp. 1-15 (2017).

(Continued)

*Primary Examiner* — Carl H Layno
*Assistant Examiner* — Manolis Pahakis
(74) *Attorney, Agent, or Firm* — Lewis & Reese, PLLC

(57) ABSTRACT

Techniques for steering of target poles formed by implantable electrodes in a stimulator device are disclosed. The steering technique modifies the relative amplitude of target poles once they are steered to an electrode array boundary. Once a target pole is steered to an electrode array boundary, further steering in the direction of that boundary results in a gradual decrease in the relative amplitude of that target pole. Eventually, continued steering in that direction will cause that target pole to disappear. Thus, in the case of a target tripole, continued steering will eventually cause the target tripole to be automatically converted into a target bipole. In another example of steering, target poles defined linearly in one direction can be split in an orthogonal direction to create a target pole configuration that is two-dimensional.

18 Claims, 16 Drawing Sheets

(51) Int. Cl.
*A61N 1/04* (2006.01)
*A61N 1/05* (2006.01)

(56) References Cited

U.S. PATENT DOCUMENTS

| | | | |
|---|---|---|---|
| 8,594,797 B2* | 11/2013 | Lee | A61N 1/3616 607/46 |
| 8,606,362 B2 | 12/2013 | He et al. | |
| 8,620,436 B2 | 12/2013 | Parramon et al. | |
| 8,644,947 B2 | 2/2014 | Zhu et al. | |
| 8,798,759 B2 | 8/2014 | Goetz et al. | |
| 8,812,124 B2* | 8/2014 | Lee | A61N 1/36185 607/59 |
| 8,825,169 B2 | 9/2014 | Zhu et al. | |
| 8,868,196 B2* | 10/2014 | Lee | A61N 1/36185 607/59 |
| 8,909,350 B2* | 12/2014 | Lee | A61N 1/37247 607/45 |
| 9,014,820 B2* | 4/2015 | Lee | A61N 1/37247 607/117 |
| 9,259,574 B2 | 2/2016 | Aghassian et al. | |
| 9,387,334 B2 | 7/2016 | Lee et al. | |
| 9,656,090 B2 | 5/2017 | Goetz | |
| 9,764,141 B2* | 9/2017 | Moffitt | A61N 1/36189 |
| 9,814,880 B2* | 11/2017 | Hershey | A61N 1/36071 |
| 9,993,646 B2* | 6/2018 | Parramon | A61N 1/36071 |
| 10,493,276 B2* | 12/2019 | Moffitt | A61N 1/0551 |
| 2008/0183256 A1 | 7/2008 | Keacher | A61N 1/37247 607/116 |
| 2010/0057165 A1* | 3/2010 | Moffitt | A61N 1/36071 607/46 |
| 2010/0057177 A1* | 3/2010 | Moffitt | A61N 1/0553 607/117 |
| 2011/0077717 A1* | 3/2011 | Poletto | A61N 1/3616 607/60 |
| 2012/0016453 A1* | 1/2012 | Feler | A61N 1/36071 607/117 |
| 2012/0239115 A1* | 9/2012 | Lee | A61N 1/37247 607/59 |
| 2012/0302912 A1* | 11/2012 | Moffitt | A61N 1/37235 600/554 |
| 2013/0116751 A1* | 5/2013 | Moffitt | A61B 34/10 607/60 |
| 2013/0172956 A1* | 7/2013 | Goddard | A61N 1/37241 607/59 |
| 2014/0277267 A1* | 9/2014 | Vansickle | A61N 1/36185 607/46 |
| 2015/0080982 A1 | 3/2015 | Funderburk | |
| 2015/0231402 A1 | 8/2015 | Aghassian | |
| 2015/0360038 A1 | 12/2015 | Zottola et al. | |
| 2016/0082261 A1* | 3/2016 | Moffitt | A61N 1/37247 607/46 |
| 2016/0082265 A1* | 3/2016 | Moffitt | A61N 1/36071 607/46 |
| 2016/0144183 A1 | 5/2016 | Marnfeldt | |
| 2018/0056068 A1* | 3/2018 | Zhang | A61N 1/36185 |
| 2018/0056078 A1 | 3/2018 | Kashyap | |
| 2018/0071513 A1 | 3/2018 | Weiss et al. | |
| 2018/0071520 A1 | 3/2018 | Weerakoon et al. | |
| 2018/0085583 A1* | 3/2018 | Zhang | A61N 1/36092 |
| 2019/0175915 A1* | 6/2019 | Brill | A61N 1/0476 |
| 2020/0230410 A1* | 7/2020 | Zhang | G16H 20/30 |
| 2020/0254256 A1* | 8/2020 | Moffitt | A61N 1/36178 |

OTHER PUBLICATIONS

E. Viezi et al., "Spinal Cord Stimulation (SCS) with Anatomically Guided (3D) Neural Targeting Shows Superior Chronic Axial Low Back Pain Relief Compared to Traditional SCS—LUMINA Study," Pain Medicine, pp. 1-15 (2017).

M. Moffit et al., A Novel 3-Dimensional Algorithm for Model-Based Programming in Spinal Cord Stimuation (SCS): Illumina-3D™, presentation (2013).

* cited by examiner

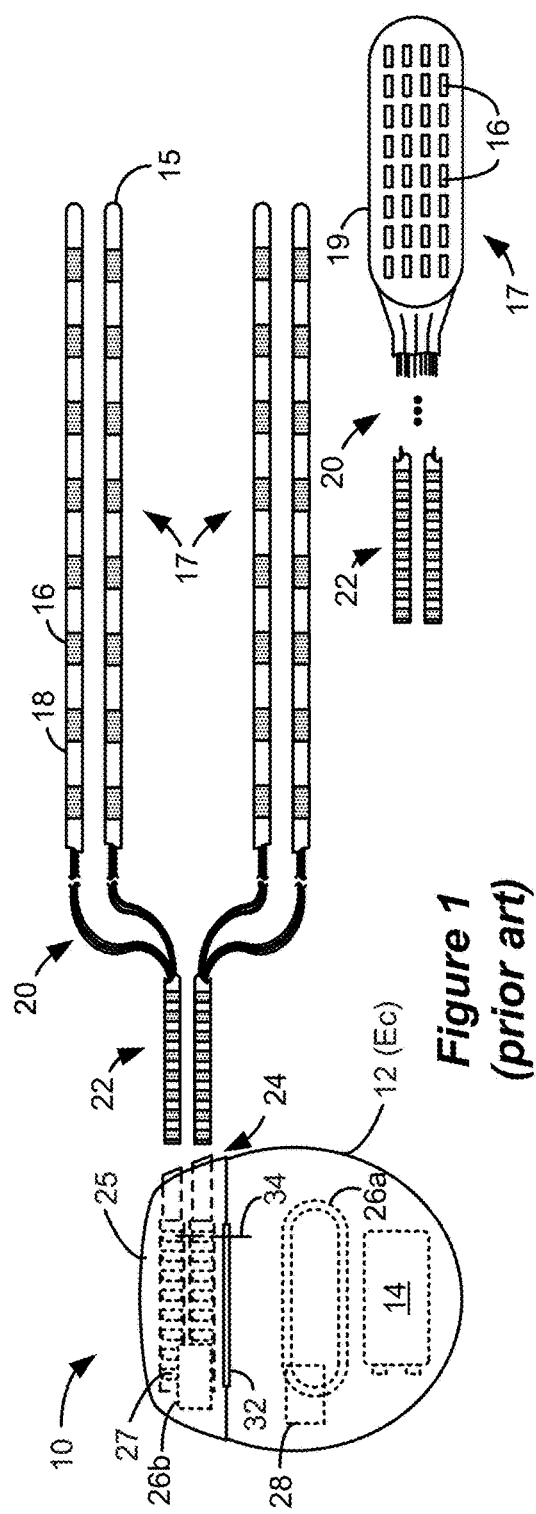
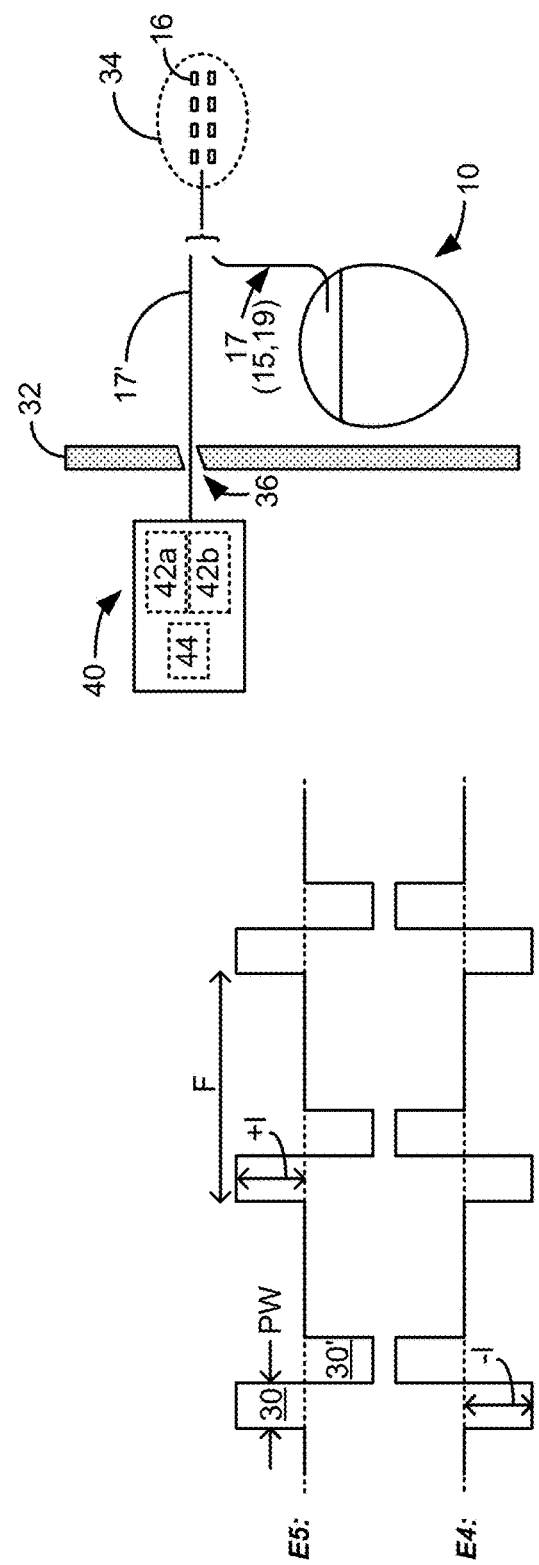
*Figure 1 (prior art)*
*Figure 2 (prior art)*
*Figure 3 (prior art)*

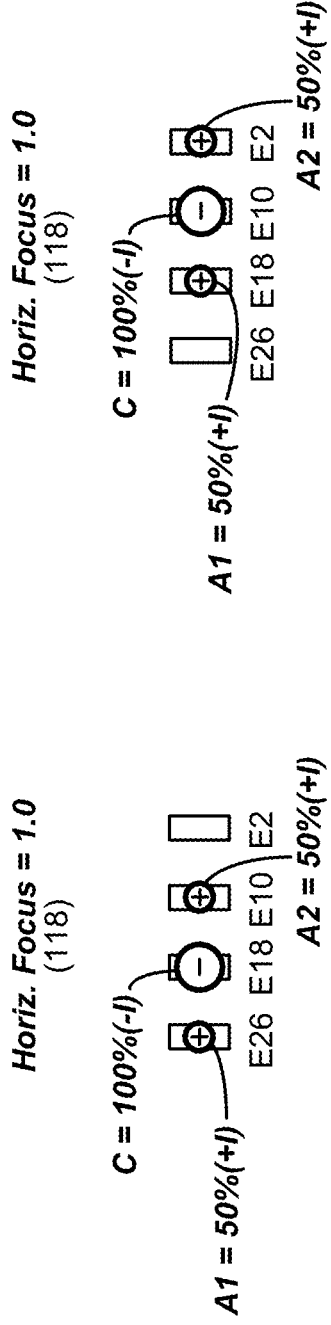
Figure 12A
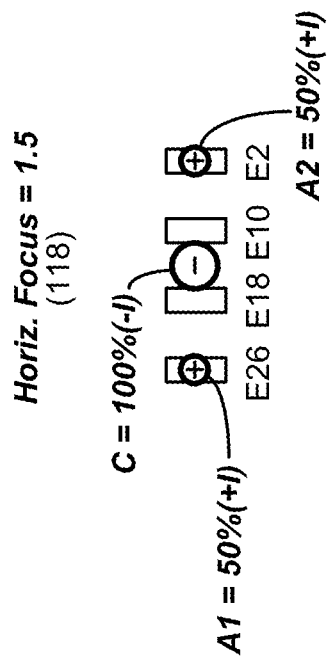
Figure 12B
Figure 12C

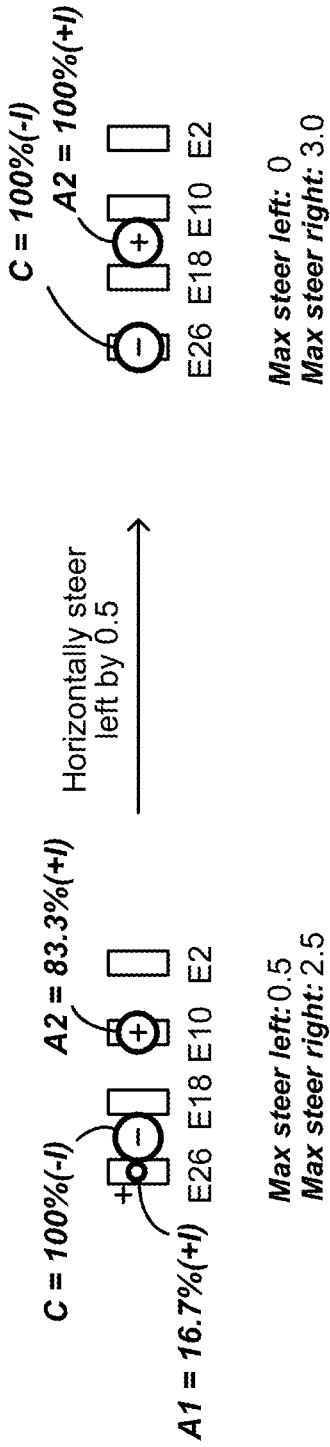

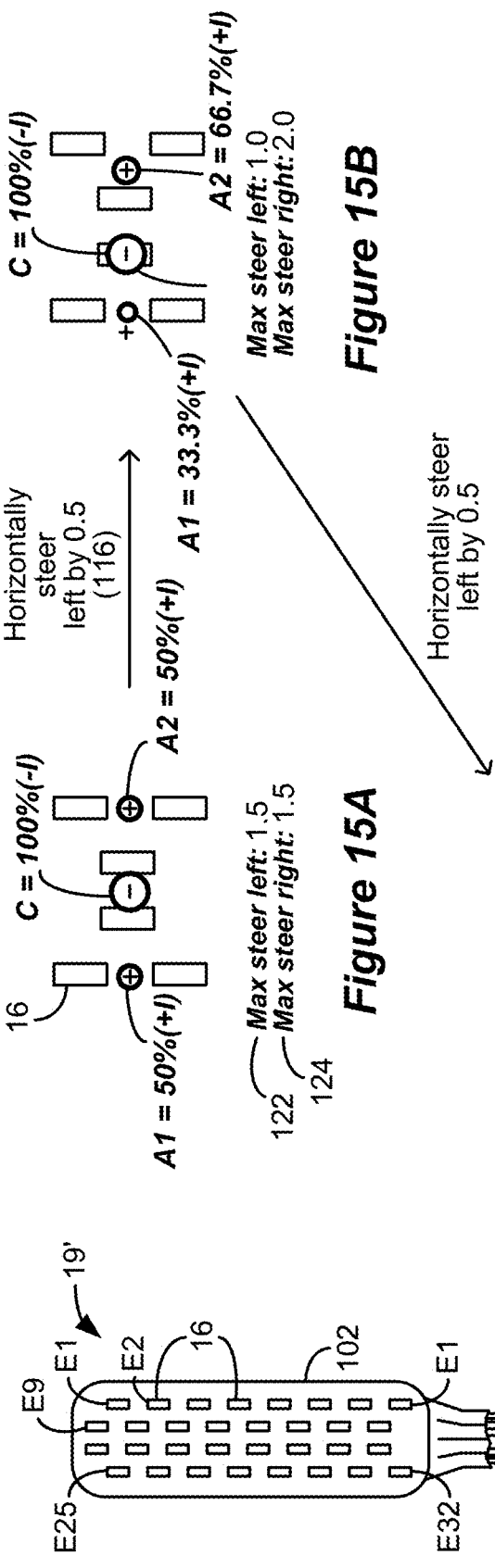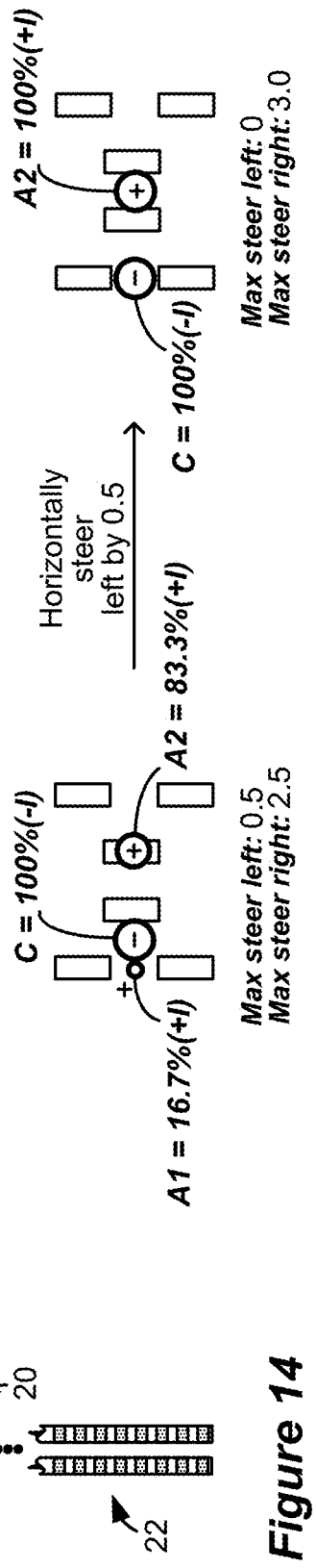

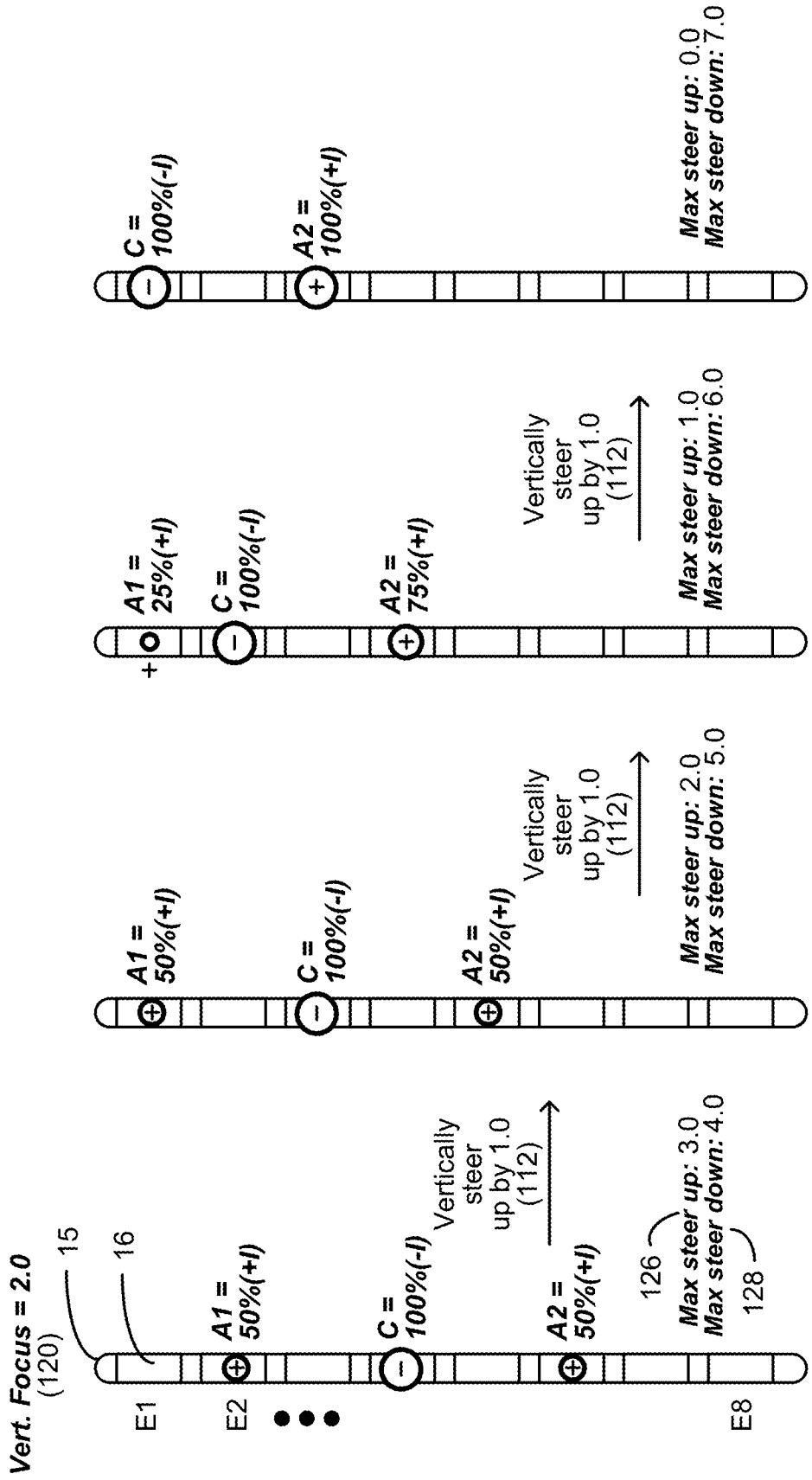

STEERING OF TARGET POLES IN AN ELECTRODE ARRAY IN A PULSE GENERATOR SYSTEM

CROSS REFERENCE TO RELATED APPLICATIONS

This is a non-provisional of U.S. Provisional Patent Application Ser. No. 62/598,114, filed Dec. 13, 2017, to which priority is claimed, and which is incorporated herein by reference in its entirety.

FIELD OF THE INVENTION

This application relates to Implantable Medical Devices (IMDs), and more specifically to steering of current between implantable electrodes.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to tissue-stimulating electrodes 16 via one or more electrode leads that form an electrode array 17. For example, one or more percutaneous leads 15 can be used, in which ring-shaped electrodes 16 are carried on a flexible body 18, which also houses the individual lead wires 20 coupled to each electrode 16. In another example, a paddle lead 19 having electrodes 16 positioned on one of its generally flat surfaces also forms an electrode array 17. The lead wires 20 are coupled to proximal contacts 22, which are insertable into lead connectors 24 fixed in a header 25 on the IPG 10, which header can comprise an epoxy for example. Once inserted, the proximal contacts 22 connect to header contacts 27 within the lead connectors 24, which are in turn coupled by feedthrough pins 34 through a case feedthrough 32 to circuitry within the case 12, although these details aren't shown.

In the illustrated IPG 10, there are thirty-two electrodes (E1-E32), split between four percutaneous leads 15, or contained on a single paddle lead 19, and thus the header 25 may include a 2×2 array of eight-electrode lead connectors 24. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning the left and right of the patient's spinal column. The proximal contacts 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected the case 12 in other IPG solutions. The goal of SCS therapy is to provide electrical stimulation from the electrodes 16 to alleviate a patient's symptoms, such as for example chronic back pain.

IPG 10 can include an antenna 26a allowing it to communicate bi-directionally with a number of external devices discussed subsequently. Antenna 26a as shown comprises a conductive coil within the case 12, although the coil antenna 26a can also appear in the header 25. When antenna 26a is configured as a coil, communication with external devices preferably occurs using near-field magnetic induction. IPG 10 may also include a Radio-Frequency (RF) antenna 26b. In FIG. 1, RF antenna 26b is shown within the header 25, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (current I, although a voltage amplitude V can also be used); the frequency (F) and pulse width (PW) of the pulses; the electrodes 16 activated to provide such stimulation; and the polarity of such active electrodes, i.e., whether active electrodes are to act as anodes (that source current to the tissue) or cathodes (that sink current from the tissue). These and possibly other stimulation parameters taken together comprise a stimulation program that the IPG 10 can execute to provide therapeutic stimulation to a patient.

In the example of FIG. 2, electrode E5 has been selected as an anode (during its first phase 30), and thus provides pulses which source a positive current of amplitude +I to the tissue. Electrode E4 has been selected as a cathode (again during first phase 30), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time, as discussed subsequently.

The pulses as shown in FIG. 2 are biphasic, comprising a first phase 30, followed quickly thereafter by a second phase 30' of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30 and discharge (have its charge recovered) during the second phase 30'. In the example shown, the first and second phases 30 and 30' have the same duration and amplitude (although of opposite polarities), which ensures the same amount of charge during both phases, and thus hopefully full recovery of charge on any capacitance such as the DC-blocking capacitors. However, the second phase 30' may also be charged balance with the first phase 30 if the product of the amplitude and durations of the two phases are equal, as is well known. The width of each pulse, PW, is shown as comprising the duration of first pulse phase 30, although pulse width could also refer to the total duration of the first and second pulse phases 30 and 30' as well. Although not shown in FIG. 2, an interphase period during which no current is driven can intervene between the first and second phases 30 and 30'.

IPG 10 includes stimulation circuitry 28 (FIG. 1) that can be programmed to produce the stimulation pulses at the electrodes as defined by the stimulation program. Stimulation circuitry 28 can for example comprise the circuitry described in U.S. Patent Application Publications 2018/0071513 and 2018/0071520, or described in U.S. Pat. Nos. 8,606,362 and 8,620,436. These references are incorporated herein by reference in their entireties.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue 32 at a target location 34, such as within the spinal column as explained earlier. The proximal ends of the trial electrode arrays(s) 17' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial electrode arrays 17' are explanted, and a full IPG 10 and a permanent electrode array 17 (e.g., one or more percutaneous 15 or paddle 19 lead(s)) are implanted as described above; if unsuccessful, the trial electrode array 17' is simply explanted.

Like the IPG 10, the ETS 40 can include one or more antennas to enable bi-directional communications with external devices, as shown in FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce stimulation with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, preferably including means for entering commands (e.g., buttons or selectable graphical icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which are capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which may depend on the GUI selections the clinician has previously made. FIG. 5 shows the GUI 64 at a point allowing for the manual setting of stimulation parameters for the patient. To the left a program interface 72 is shown, which as explained further in the '038 Publication allows for naming, loading and saving of stimulation programs for the patient. Shown to the right is a stimulation parameters interface in which specific stimulation parameters can be defined for a stimulation program. Values for stimulation parameters relating to the shape of the waveform (amplitude I), pulse width (PW), and frequency (F) are shown in a waveform parameter interface 84, including buttons the clinician can use to increase or decrease these values. Amplitude I sets the value of the total anodic current +I one or more selected anode electrodes will source to the patient, and the value of the total cathodic current −I one or more selected anode electrodes will sink from the patient.

Stimulation parameters relating to the electrodes 16 are made adjustable in an electrode parameter interface 86. Electrodes are manually selectable in a leads interface 92 that displays a graphical representation of the electrode array 17 or 17' (one or more permanent or trial leads) that has been implanted in a particular patient (a paddle lead 19 is shown as one example). A cursor 94 (or other selection means such as a mouse pointer) can be used to select a particular electrode in the leads interface 92. Buttons in the electrode parameter interface 86 allow the selected electrode (including the case electrode, Ecase) to be designated as an anode, a cathode, or off. The electrode parameter interface 86 further allows the relative amount of total anodic or cathodic current +I or −I of the selected electrode to be specified in terms of a percentage, X. This is particularly useful if more than one electrode is to act as an anode or cathode at a given time, as explained in the '038 Publication.

An advanced menu 88 can be used (among other things) to define the relative durations and amplitudes of the pulse phases 30 and 30', and to allow for other more advance modifications, such as setting of a duty cycle (on/off time) for the stimulation pulses, a ramp-up time over which stimulation reaches its programmed amplitude (I), various parameters relating to the issuance of a burst of pulses, etc. A mode menu 90 allows the clinician to choose different modes for determining stimulation parameters.

While GUI 64 is shown as operating in the clinician programmer 50, the user interface of the external controller 45 may provide similar functionality because the external controller 45 can include much of the same hardware and software programming as the clinician programmer.

SUMMARY

In a first example, a system and related methods are disclosed, which may comprise: an external device comprising a graphical user interface (GUI) for programming an implantable stimulator device, wherein the implantable stimulator device comprises a plurality of electrodes configured to contact a patient's tissue, the plurality of electrodes comprising an electrode array, wherein the external device comprises controller circuitry programmed to execute a steering algorithm, and wherein the steering algorithm is configured to: receive, via the GUI of the external device, one or more inputs to steer within the electrode array a plurality of target poles that prescribe stimulation at one or more of the plurality of electrodes; steer the target poles in a direction toward an electrode array boundary; and, if a first of the target poles has a position at the electrode array boundary and the target poles are steered an amount further in that direction, keep the first target pole at the position and automatically reduce an amplitude of the first target pole.

The plurality of target poles may comprise a target pole configuration in which each target pole is defined by a position within the electrode array, a polarity, and a current amplitude. The GUI may be configured to receive an input associated with a total anodic and cathodic current amplitude to be shared between the target poles. The controller circuitry may be further programmed with and configured to execute an electrode configuration algorithm, wherein the electrode configuration algorithm is configured to automatically determine, from the target pole configuration, active electrodes, their polarities, and their current amplitudes that prescribe the stimulation at the one or more of the plurality of electrodes.

The steering algorithm may be further configured to: if the target poles are steered the amount further in the direction, steer all second target poles different from the first target pole by the amount in the direction. One of the second target poles may comprise a central target pole. The target poles may a focus distance in the direction relative to the central target pole, and the steering algorithm may be further configured to: automatically reduce the amplitude of the first target pole based on a distance between the first target pole and the central target pole and the focus distance.

The plurality of target poles may comprise a tripole, wherein the first target pole comprises an anode, a second of the target poles comprises a cathode, and a third of the target poles comprises an anode, and the steering algorithm may be further configured to: if a first of the target poles has a position at the electrode array boundary and the target poles are steered an amount further in that direction, automatically reduce an amplitude of the first target pole by a first value and automatically increase an amplitude of the third target pole by a second value. The first value and the second value may be equal.

The steering algorithm may be further configured to: if the target poles are steered an amount still further in the direction such that the central target pole is positioned at the electrode array boundary, remove the first target pole or set its amplitude to zero. The plurality of target poles may comprise a tripole, and the steering algorithm may be further configured to: if the target poles are steered the amount still further in the direction such that the central target pole is positioned at the electrode array boundary, modify the target poles from the tripole to a bipole.

The system may further comprise the implantable stimulator device. The implantable stimulator device may comprise a fully-implantable implantable pulse generator. The implantable stimulator device may also comprise an external trial stimulator coupled to the electrode array, wherein the electrode array is implantable in a patient.

The electrode array may comprise a horizontal dimension that is smaller than a vertical dimension. The target poles may comprise a horizontal target pole configuration. The electrode array may comprise a paddle lead. The electrode array may comprises one or more percutaneous leads.

In a second example, a non-transitory computer readable media is disclosed which may comprise instructions executable on an external device comprising a graphical user interface (GUI) for programming an implantable stimulator device, wherein the implantable stimulator device comprises a plurality of electrodes configured to contact a patient's tissue, the plurality of electrodes comprising an electrode array, wherein the instructions comprise a steering algorithm, wherein the steering algorithm when executed is configured to: receive, via the GUI of the external device, one or more inputs to steer within the electrode array a plurality of target poles that prescribe stimulation at one or more of the plurality of electrodes; steer the target poles in a direction toward an electrode array boundary; and, if a first of the target poles has a position at the electrode array boundary and the target poles are steered an amount further in that direction, keep the first target pole at the position and automatically reduce an amplitude of the first target pole.

In a third example, a system and related methods are disclosed, which may comprise: an external device comprising a graphical user interface (GUI) for programming an implantable stimulator device, wherein the implantable stimulator device comprises a plurality of electrodes configured to contact a patient's tissue, the plurality of electrodes comprising an electrode array, wherein the external device comprises controller circuitry programmed to execute a steering algorithm, wherein the steering algorithm is configured to: receive, via the GUI of the external device, one or more first inputs to steer within the electrode array a plurality of target poles that prescribe stimulation at one or more of the plurality of electrodes, wherein the target poles are defined along a first axis in the electrode array and comprise first target poles and a central target pole; and wherein the one or more first inputs comprises one or more second inputs to automatically split at least each first target pole in a direction orthogonal to the first axis to form at least one associated second target pole.

The steering algorithm may be further configured in response to the one or more second inputs to: split each first target pole and the central target pole in a direction orthogonal to the first axis to form at least one associated second target pole. The one or more second inputs may comprise a first option to define a distance between each first target pole and each of its at least one associated second target pole. The one or more second inputs may also comprise a second option to define an amount of current amplitude to be moved from each first target pole to its at least one associated second target pole. The second option may allow all current amplitude to be moved from each first target pole to its at least one associated second target pole.

The steering algorithm may be further configured in response to the one or more second inputs to: split at least each first target pole in a direction orthogonal to the first axis to form a pair of associated ones of the second target poles on both sides of the first axis. The steering algorithm may also be further configured in response to the one or more second inputs to: split at least each first target pole in a direction orthogonal to the first axis to form a single second target pole to one side of the first axis. The target poles may comprise a tripole.

The plurality of target poles may comprise a target pole configuration in which each target pole is defined by a position within the electrode array, a polarity, and a current amplitude. The GUI may be configured to receive an input associated with a total anodic and cathodic current amplitude to be shared between the target poles. The controller circuitry may be further programmed with and configured to execute an electrode configuration algorithm, wherein the electrode configuration algorithm is configured to automatically determine, from the target pole configuration, active electrodes, their polarities, and their current amplitudes that prescribe the stimulation at the one or more of the plurality of electrodes.

The system may further comprise the implantable stimulator device. The implantable stimulator device may comprise a fully-implantable implantable pulse generator. The implantable stimulator device may also comprise an external trial stimulator coupled to the electrode array, wherein the electrode array is implantable in a patient.

The electrode array may comprise a paddle lead. The electrode array may also comprise one or more percutaneous leads.

In a fourth example, a non-transitory computer readable media is disclosed which may comprise instructions executable on an external device comprising a graphical user interface (GUI) for programming an implantable stimulator device, wherein the implantable stimulator device comprises a plurality of electrodes configured to contact a patient's tissue, the plurality of electrodes comprising an electrode array, wherein the instructions comprise a steering algorithm, wherein the steering algorithm when executed is configured to: receive, via the GUI of the external device, one or more first inputs to steer within the electrode array a plurality of target poles that prescribe stimulation at one or more of the plurality of electrodes, wherein the target poles are defined along a first axis in the electrode array and comprise first target poles and a central target pole; and wherein the one or more first inputs comprises one or more second inputs to automatically split at least each first target pole in a direction orthogonal to the first axis to form at least one associated second target pole.

BRIEF DESCRIPTION OF THE DRAWINGS

FIG. 1 shows an Implantable Pulse Generator (IPG), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

FIGS. 7-9C show an electrode configuration algorithm useful to determine active electrodes, polarities, and relative amplitudes given the location, polarities, and relative amplitudes of the target poles.

FIGS. 12A-12C show a horizontal target tripole, and shows how steering of the tripole is conventionally constrained by the boundary of the electrode array.

FIGS. 13A-13D show a steering algorithm that allows the target tripole of FIG. 12C to be steered with automatic modification despite being conventionally constrained.

FIGS. 14-15D show operation of the steering algorithm using a modified paddle lead.

FIGS. 16A-16D show target pole definition and operation of the steering algorithm in a single percutaneous lead.

DETAILED DESCRIPTION

Figure 5:
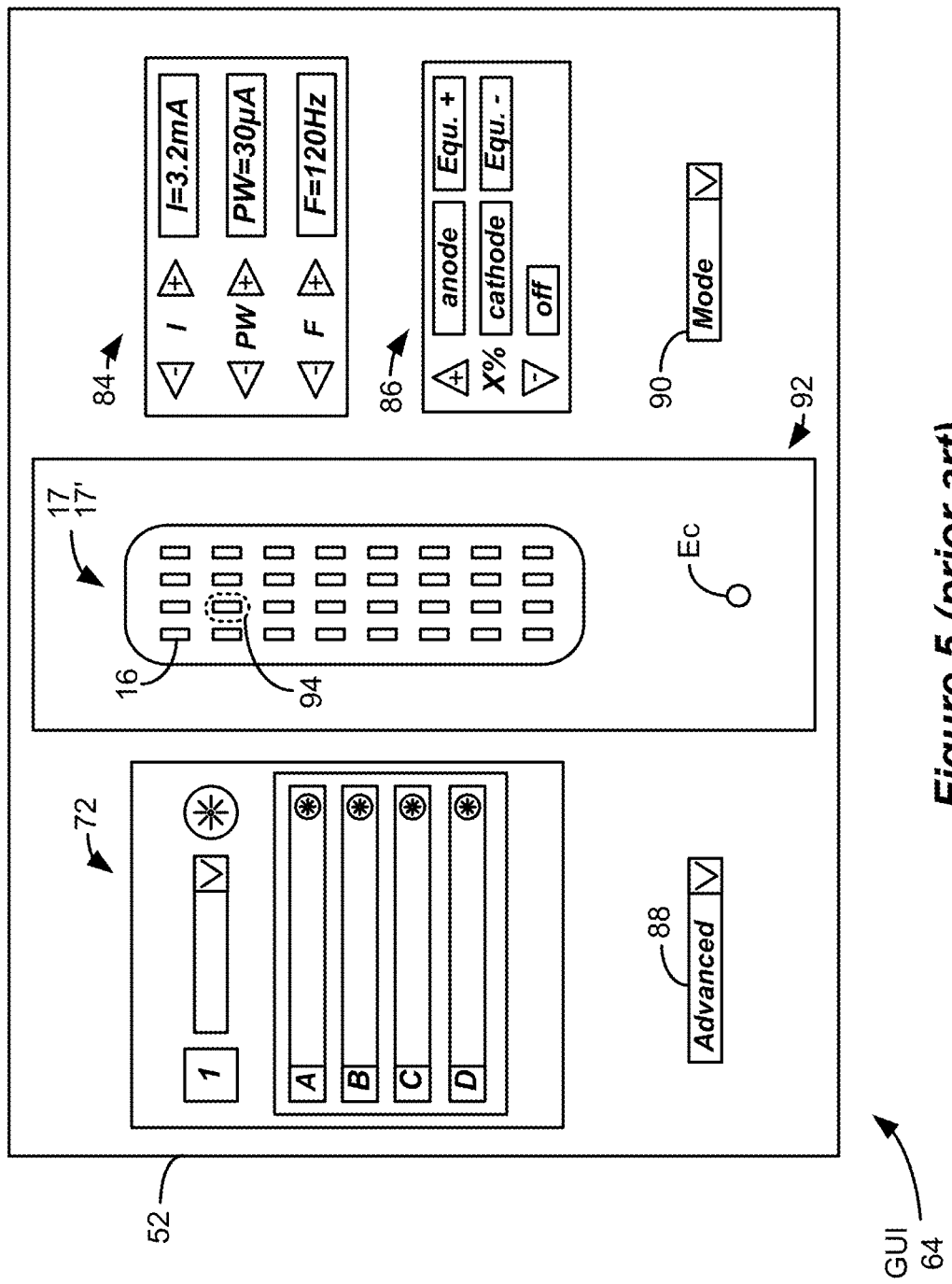
FIG. 5 shows a Graphical User Interface (GUI) of a clinician programmer external device for setting or adjusting stimulation parameters, in accordance with the prior art.
Figure 6:
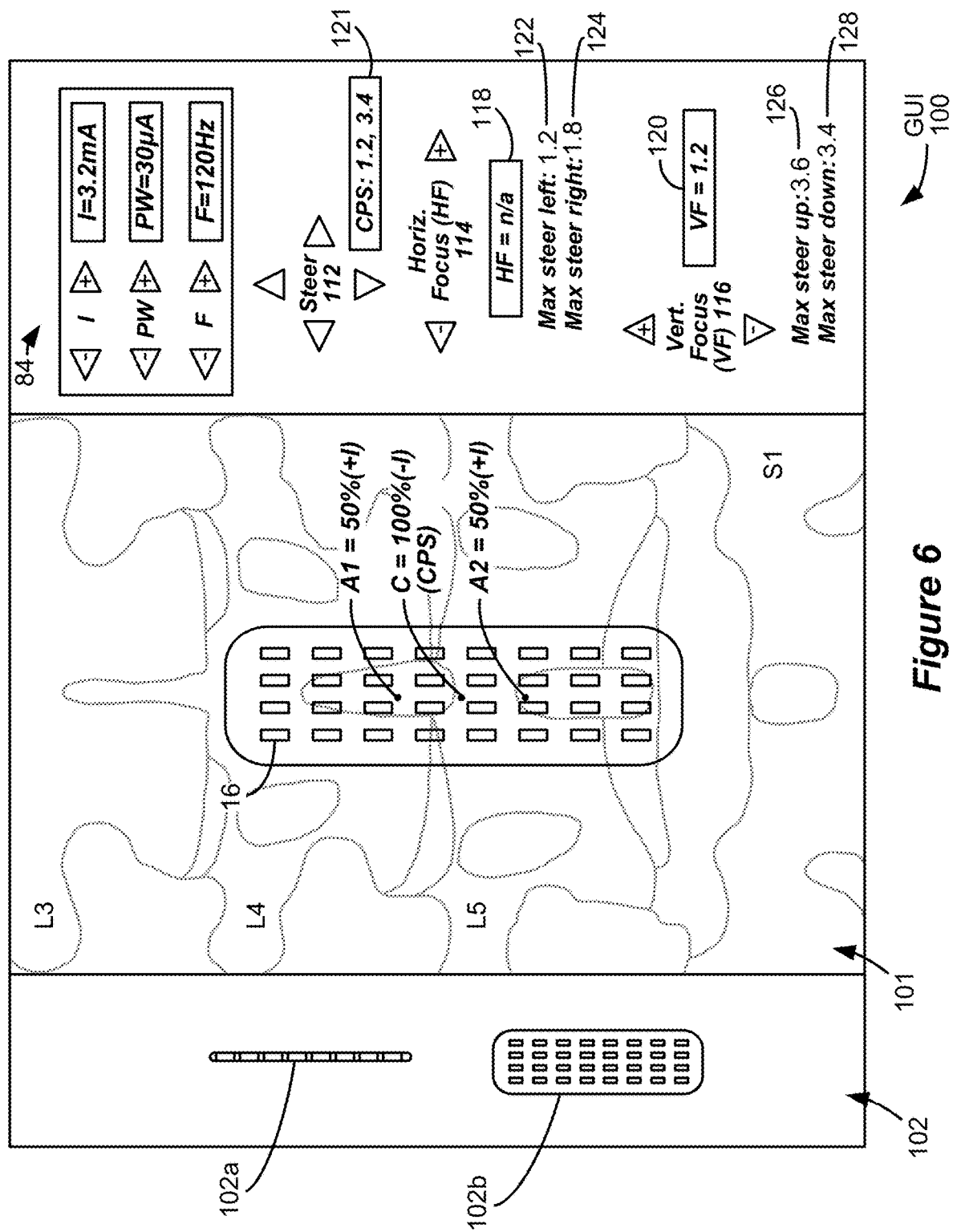
FIG. 6 shows an improved GUI allowing for improved definition and steering of target poles in an electrode array such as a paddle lead.

FIG. 6 shows another GUI 100 that can be used to set a stimulation program for a patient including inventive aspects that are discussed later. As described further below, GUI 100 allows a user to steer target poles (described further below) around an electrode array 17 or 17', which provides a more-automated and convenient means for setting and adjusting a stimulation program compared to the more manual means provided by GUI 64 of FIG. 5. GUI 100 can be arrived at for example as a selection under the mode menu 90 of the GUI 64. Alternatively, GUI 100 can comprise part of GUI 64, or aspects of both GUIs can be integrated to a desired extent. Like GUI 64, GUI 100 is rendered by execution of clinician programmer software 66 on the clinician programmer 50, and may similarly be executed in an external controller 45 or other external device capable of programming the IPG 10 or ETS 40.

GUI 100 may include a fluoroscopic image 101, which shows one or more implanted leads relative to anatomical structures, such as vertebrae (L3, L4, L5, and S3 are shown). A user can select a graphical representation of the implanted electrode lead(s) from left side panel 102, which includes representations of various types of leads such as a 1×8-electrode percutaneous lead representation 102a, and a 4×8-electrode paddle lead representation 102b. More than these two lead types and leads with different numbers of electrodes may also be represented. The fluoroscopic image 101 may contain more than one lead representation, for example, left and right percutaneous leads, to match the number of leads implanted in the patient. The user can select (e.g., by dragging) the appropriate lead representation(s) 102 onto the fluoroscopic image 101 and manipulate its size and orientation until it aligns with the implanted electrode lead in the fluoroscopic image 101. Because the lead representations 102 are programmed with appropriate electrode size, shape, and spacing for each of the leads, the positioning of a lead representation on the fluoroscopic image 101 relates the locations of the electrodes to the anatomical structures in the image.

Such visualization assists a user to set the location of a desired stimulation field by defining the locations, polarities, and relative amplitudes of one or more anode target poles, A, and one or more cathode target poles C. In the example shown, a target tripole is shown having a single cathode target pole C and two flanking anode target poles A1 and A2. Notice that the specified target poles do not necessarily correspond to the positions of the physical electrodes 16 in the lead(s), and can occur at any random location. In the example shown, the single cathode target pole C receives all of the total cathodic current −I that will be sunk from the patient's tissue (100%*−I). Each of the anode target poles A1 and A2 receives half of the total anodic current +I (50%*+I) that will be sourced to the patient's tissue. Tripolar stimulation can be preferred, as recruitment of nerve fibers tends to happen proximate to the cathode target pole between the anode target poles.

Although not shown, realize that the GUI 100 can allow the user to select a particular configuration for the target poles, such as a tripole (as shown), a bipole, or any other configuration of one or more anode target poles and one or more cathode target poles. Further, the GUI 100 can allow the user to set or input the position of the target poles; the polarity of the target poles, whether anodic or cathodic; and the relative amplitudes of the target poles—that is, the percentages of total anodic current +I or total cathodic current −I that each target pole will provide.

The relative amplitudes of the target poles may default to logical percentages based on the target pole configuration chosen. For example, if the user has selected a tripole for the target poles, it may be assumed that the cathode target pole C will (perhaps even must) receive 100% of the total cathodic current −I, while the anode target poles will evenly split the total anodic current, each receiving 50%*+I, alleviating the user from having to specifically choose these relative amplitudes. Note also that GUI 100 may also include the waveform parameter interface 84 discussed earlier, allowing basic waveform parameters such as amplitude I (total anodic and cathodic current +I and −I), pulse width (PW) and frequency (F) to be set.

After the position, polarity, and relative amplitude of each of the target poles is specified, an electrode configuration algorithm 110 preferably automatically operates in the clinician programmer 50 (or external controller 45) to determine an electrode configuration—i.e., to determine which physical electrodes 16 should be activated, and with what polarities and relative amplitudes, to best approximate creation of the desired target poles in the patient's tissue. Generating an electrode configuration from the desired positions, polarities, and relative amplitudes of target poles is explained in detail in U.S. Pat. No. 8,412,345, and so is only briefly described here.

Figure 7:
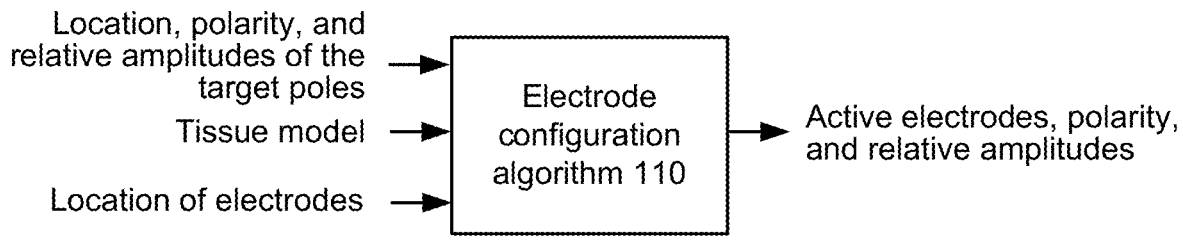

FIG. 7 shows an example of the inputs and outputs of electrode configuration algorithm 110 operable in the relevant external device, which may run automatically or upon a user selection in GUI 100. The inputs include the desired location of the target poles (which again need not correspond to physical electrode positions); the polarity of the target poles; the relative amplitudes of the target poles (which again can be set in GUI 100 or assumed to be of logical values); a model of the tissue environment; and the location of the physical electrodes 16 in the electrode array 17 or 17'.

Figure 8:
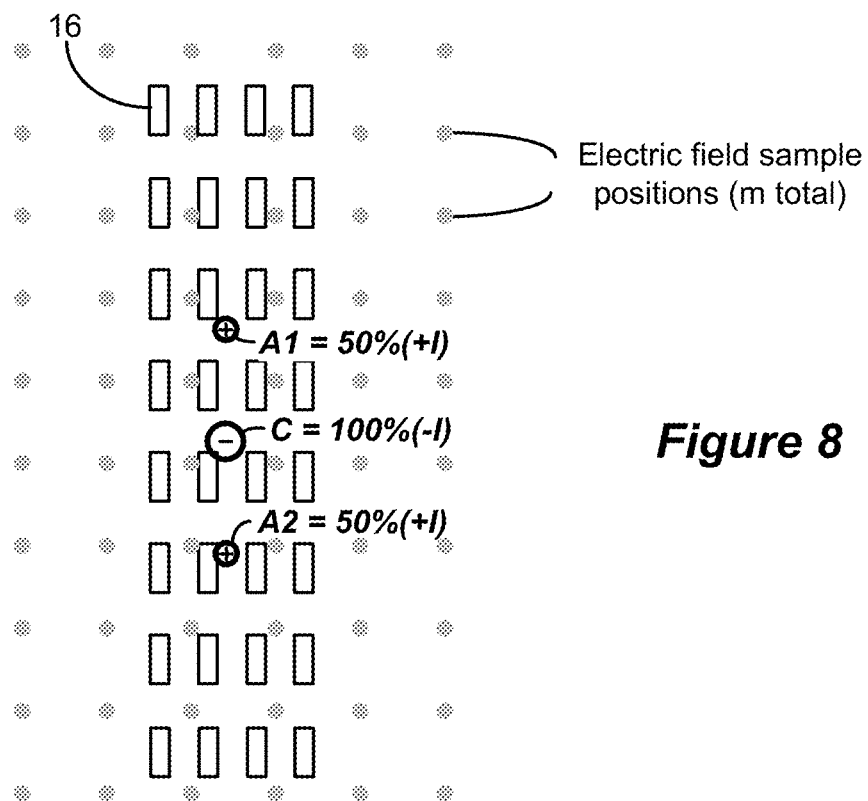

The tissue model (such as a finite element model) can be used to evaluate the electric field that would be generated as a result of stimulation at the target poles (i.e., if actual electrodes were present at those positions), and may take into account the different conductivities and sizes of anatomical structures in the tissue, such as white matter, gray matter, cerebral spinal fluid, the dura, and vertebral bone in the area of the target poles. Using such modeling of the tissue, and as shown in FIG. 8, a voltage $V_m$ that would be induced at each of m electric field sample positions in the tissue is determined that would result from stimulation at the target poles. The modeled voltages at each of the m sample positions can be represented as a m×1 vector, φ (FIG. 9A).

The tissue model is also used to determine voltages $U_{m,n}$ that would be induced at the m sample positions as a result of stimulation using n physical electrode combinations. While the modeled electrode combinations can include any number of combinations of the electrodes (e.g. bipoles, tripoles, etc.), in one simple example, the n electrode combinations are bipoles that are incremented along the electrode array 17 or 17'. For example, a first electrode combination can comprise selecting E1 as a sole cathode and E2 as a sole anode; a second electrode combination can comprise selecting E2 as a sole cathode and E3 as a sole anode, etc. (Thus, in this example, n equals the number of electrodes in the electrode array 17 or 17' minus one). Simulation at the various electrode combinations occurs assuming the same current amplitude. The modeled voltages $U_{m,n}$ can be represented as a m×n transfer matrix, A (FIG. 9B). Thus, $U_{1,1}$ comprises the voltage at sample position 1 simulating stimulation at electrode combination 1 (e.g., E1/E2); $U_{1,2}$ comprises the voltage at sample position 1 simulating stimulation at electrode combination 2 (e.g., E2/E3); $U_{2,1}$ comprises the voltage at sample position 2 simulating stimulation at electrode combination 1 (e.g., E1/E2), etc. Any number of electrode combinations n and sample positions m can be modeled, which would increase the size of the transfer matrix A and promote higher solution accuracy, although a larger transfer matrix A is also more computationally difficult.

The electrode combinations that would induce voltages at the m sample positions that best match those generated as a result of stimulation at the target poles (φ) can be determined by solving for a vector j that minimizes the equation $|\varphi - A*j|^2$, where j comprises a 1×n matrix indicating a weight $X_n$ that each nth electrode combination plays in forming the desired electric field. Such solution involves inverting the transfer matrix A ($A^{-1}$), such that $j=A^{-1}*\varphi$. The weights of the electrode combinations in vector j can then be summed to determine a physical electrode configuration—i.e., which physical electrodes should be active, as well as their polarity and relative amplitudes—to produce the target poles' desired electric field.

For example, if electrode combination 3 (E3 as cathode and E4 as anode) is calculated to have a relative weight of 5 in vector j ($X_3=5$), and combination 4 (E4 as cathode and E5 as anode) is given a relative weight of 2 ($X_4=2$), then electrode E4 (which can't be both an anode and cathode at the same time) would operate as an anode, because a stronger weight is given to a combination in which E4 is an anode. Further, anode E4 would have a relative amplitude of 3 (i.e., the difference of the two weights $X_3-X_4$). By contrast, if electrode combination 12 (E12 as cathode and E13 as anode) is given a relative weight of 2 ($X_{12}=2$), and combination 13 (E13 as cathode and E14 as anode) is given a relative weight of 2 ($X_{13}=2$), then electrode E13 is called on to be both an anode and a cathode with equal weights; therefore electrode E13 would be inactive, because it would not significantly contribute to forming the target's poles' desired electric field.

In short, the output of the electrode configuration algorithm 110 determines an electrode configuration (active electrodes, their polarities, and their relative amplitudes) necessary to best produce the desired electric field from the specified target poles. It should be noted that the electrode configuration algorithm 110 as shown preferably results in a charge-balanced solution in which the sum of cathodic currents at selected cathodic electrodes equals 100%*−I, and in which the sum of anodic currents and selected anode electrodes equals 100%*+I.

Figure 10:
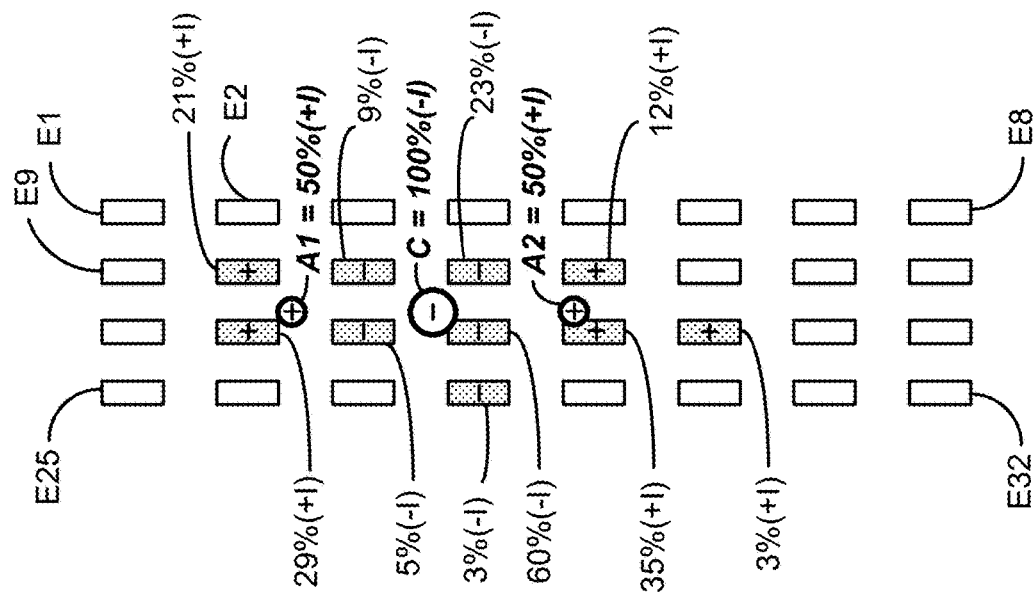
FIG. 10 shows an example of operation of the electrode configuration given a particular target pole configuration.

An example of the operation of the electrode configuration algorithm 110 is shown in FIG. 10. The target poles C, A1, and A2 as before have been set to desired positions relative to the physical electrodes and the patient's tissue and their relative amplitudes are set as before (C=100*−I, A1=A2=50%*+I), with the relative amplitudes being represented by circles of different sizes. With these target pole locations, polarities, and relative amplitudes entered into the GUI 100 of the clinician programmer 50, and using the tissue model and the location of the physical electrodes 16, the electrode configuration algorithm 110 can operate to derive an electrode configuration to best match the electric field the target poles would produce in the tissue.

Electrodes activated by the electrode configuration algorithm 110 are shaded in grey in FIG. 10, with their polarities (anodes or cathodes) specified by a plus or minus, and with a percentage or fraction of the total anodic current +I and the total cathodic current −I. Notice that electrode E20 is nearest the specified location of the cathode target pole, C. Not surprisingly then, electrode configuration algorithm 110 will likely designate this physical electrode as a cathode electrode, and given E20's proximity to the cathode target pole, this electrode will be prescribed by the algorithm with a relatively high percentage of the total cathodic current—I, e.g., 60%*−I as shown. However, other electrodes also generally proximate to the cathode target pole C will also be prescribed with significant percentages of the total cathodic current, e.g., electrode E12 receives 23%*−I. The total anodic current, split between the anode target poles A1 and A2, is likewise generally split at the electrodes proximate to these poles. For example, electrodes E10) and E18 proximate to anode target pole A1 receive 29% and 21% of +I, for a total of 50%*+I. Electrodes E21, E13, and E22 proximate to anode target pole A2 receive 35%, 12%, and 3% of +I, for a total of 50%*+I. These percentages are just examples of the type of outputs that electrode configuration algorithm 110 can derive based on the prescribed target poles.

The electrode configuration algorithm 110 as described is just one manner in which an electrode configuration can be determined or estimated from target poles. Other electrode configuration determinations can be used, which may or may not rely on tissue modeling as described.

Note that the derived electrode configuration can be transmitted along with other stimulation parameters set in waveform parameter interface 84, such as amplitude I (specifying both total anodic and cathodic current +I and −I), pulse width (PW) and frequency (F), from the external device (the clinician programmer 50 or external controller 45) to the IPG 10 or ETS 40 where the stimulation program can then be executed to form stimulation in the patient's tissue.

Figure 11:
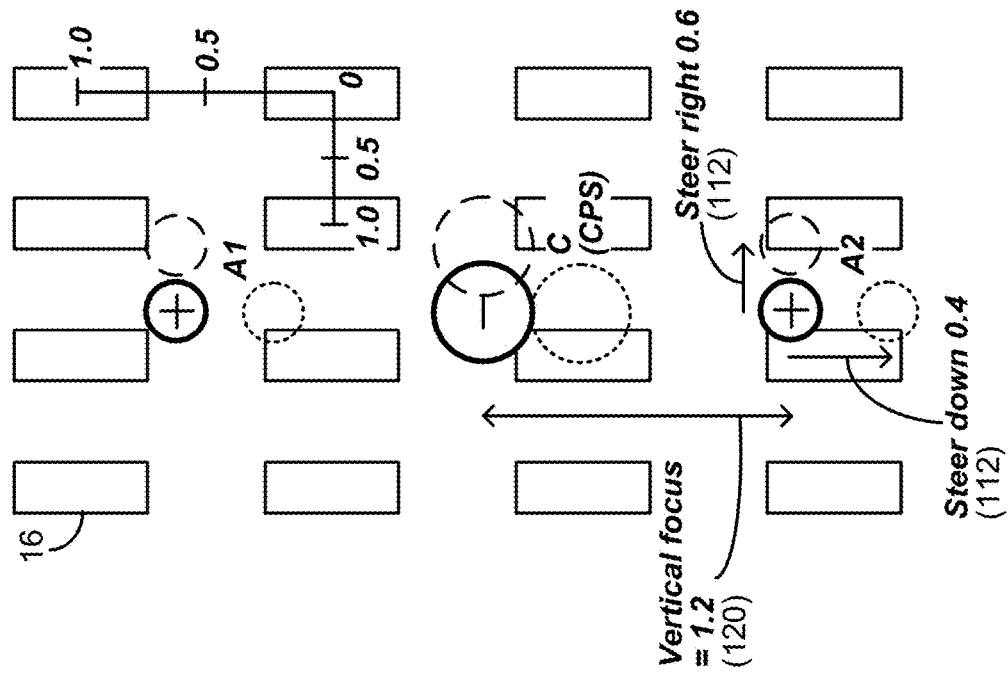
FIG. 11 shows steering of target poles in an electrode array.

Once a target pole configuration is set, it can be useful to "steer" that configuration to see if a patient's symptoms can be further improved by changing the location of the stimulation. An example of steering target poles is shown in FIG. 11. A magnified view of the target poles C, A1, and A2 from FIG. 10 is shown, as is a grid system that defines units in which the target poles can be steered up or down (vertically), and right and left (horizontally). The grid system defines a horizontal distance of 1.0 as the distance between two adjacent horizontal electrodes and a vertical distance of 1.0 as the distance between two adjacent vertical electrodes.

However, other horizontal and vertical units could be used, such as actual physical distance (e.g., in microns).

Figure 4:
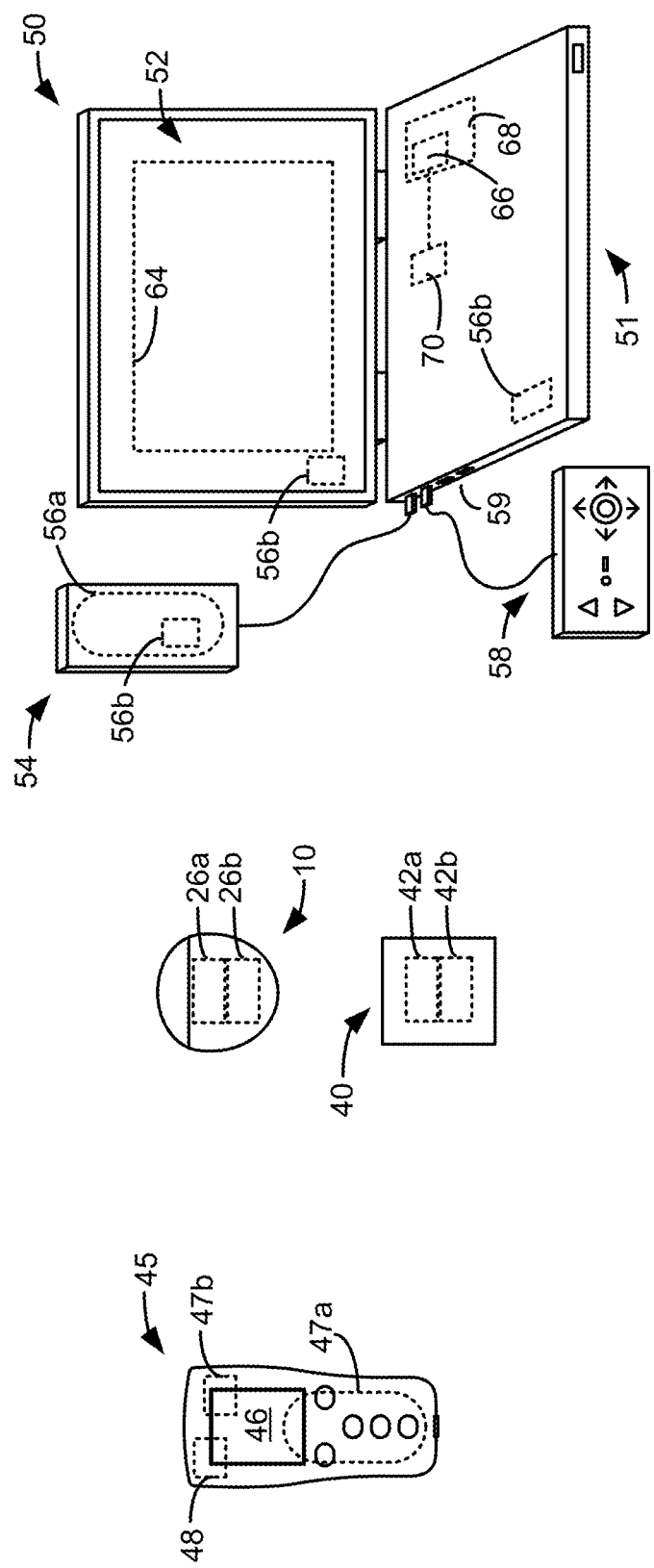
FIG. 4 shows various external devices capable of communicating with and programming stimulation in an IPG and ETS, in accordance with the prior art.

FIG. 11 shows two examples in which the target poles have been steered from their initial position: a first in which they are steered 0.6 units to the right (horizontally), and a second in which they are steered 0.4 units down (vertically). The target poles can be steered in GUI 100 using a steering interface 112 (FIG. 6), which as shown include selectable right/left and up/down, arrows. (Note also that the joystick 58 of FIG. 4 can also be used to control target pole steering). As the target poles are steered, electrode configuration algorithm 110 (FIG. 7) would recalculate the electrode configuration required to form an electric field commensurate with the new positions of the target poles. In other words, new electrodes, polarities, and relative amplitudes will be determined, although this detail isn't shown in FIG. 11. Such new electrode configuration as well as other stimulation parameters (e.g., I, PW, F) will then be transmitted to the IPG 10 or ETS 40 to gauge their effectiveness in treating the patient.

FIG. 11 also shows the "focus" of the target poles. The focus generally comprises the distance between two target poles, and in the tripole example can comprise a distance from the outer target poles (here, A1 and A2) to a central target pole (here, C). In the example shown in FIG. 11, the focus comprises a vertical focus (VF), because the target poles are aligned vertically, with the vertical focus set to a vertical distance of 1.2. Both the horizontal focus and the vertical focus of the target poles can be adjusted in the GUI 100 (FIG. 6) using focus interfaces 114 and 116, which as shown include selectable arrows to increase and decrease the focus. The value of the horizontal focus and the vertical focus are shown using indicators 118 and 120 respectively. While setting of the vertical and horizontal foci 114 and 116 can be independent, they can also be related with the value of one dictating the value of the other. This can be useful for example if the electrode array has different vertical and horizontal dimensions. For example, if the vertical dimension of the array is twice the horizontal dimension, then the vertical focus might be set at twice the horizontal focus (i.e., VF=2HF). As with steering, changing the focus will cause the electrode configuration algorithm 110 to recalculate a new electrode configuration required to form an electric field commensurate with the new positions of the target poles, which again can be transmitted to the IPG 10 or ETS 40.

It can be useful when steering target poles to consider a center point of stimulation, or CPS 121, which in the case of the illustrated target tripole would comprise the sole cathode. Note that the position of the target poles can be defined (and specified in GUI 100 of FIG. 6) by setting the position of the CPS and the horizontal or vertical focus.

Similar target pole definition, steering and focus adjustment can along the horizontal direction. For example, FIG. 12A shows a horizontal target tripole in relation to a row of electrodes 16 on the paddle lead 19 illustrated earlier. In this example, the cathode target pole C is located at E18, and anode target poles A1 and A2 are located at flanking electrodes E26 and E10. Because each anode target pole A1 and A2 is one physical electrode away from the cathode electrode, the horizontal focus (HF) equals 1.0, which can be specified and illustrated in GUI 100 (FIG. 6) at elements 114 and 118. Again, the target poles need not correspond to the location of the physical electrodes in the electrode array 17 or 17'.

In FIG. 12B, the tripole of FIG. 12A has been steered (112) one unit to the right, such that the cathode target pole C is now located at E10, and the anode target poles A1 and A2 are located at electrodes E18 and E2.

Because the target poles in FIGS. 12A and 12B correspond to the positions of physical electrodes, the electrode configuration algorithm 110 (FIG. 7) would likely simply select these physical electrodes to issue the polarity and relative amplitudes prescribed for the target poles. In other words, and taking FIG. 12A as an example, the electrode configuration algorithm 110 would likely select electrodes E26 and E10 as anode electrodes and cause each to issue an anodic current of 50%*+I, and select electrode E18 as a cathode electrode that will issue the entire cathodic current of 100%*−I. However, the electrode configuration chosen can depend on the particular implementation of the electrode configuration algorithm 110, and any mathematics or modeling it utilizes. Thus, in some examples, the electrode configuration algorithm 110 could select and activate electrodes in different rows of the electrodes array 17 or 17' to form the target poles of FIGS. 12A and 12B, although this isn't shown.

In FIG. 12C, the horizontal focus of the target tripole has been adjusted (114) to 1.5. In this example, the cathode target pole C is located midway between electrodes E18 and E10, while the target anodes A1 and A2 are located at E26 and E2 respectively. It is likely the electrode configuration algorithm 110 in this example would select electrodes E26 and E2 to operate as anode electrodes and cause each to issue an anodic current of 50%*+I. Electrode configuration algorithm 110 would probably also select electrodes E18 and E10 proximate to the cathode target pole C as cathode electrodes, and because C is midway between would likely prescribe relative amplitudes at those electrodes of 50%*−I. Again, the selected electrodes, polarities, and relative amplitudes will depend on the particulars of the electrode configuration algorithm 110.

Steering of target poles can hampered by the boundaries inherent in the size of the electrode array 17 or 17'. Particularly in the horizontal direction for the example paddle lead 19, there are not as many columns of electrodes (e.g., 4), i.e., the horizontal dimension of the electrode array is smaller than its vertical dimension. A target tripole therefore has less room to steer in this direction in this particular example. Consider again FIGS. 12A and 12B having a horizontal target tripole with a horizontal focus of one. Conventionally, this tripole can only be horizontally steered in a range between the two states shown: one in which the target tripole is defined by electrodes in the first, second, and third columns (e.g., E26, E18, and E10; FIG. 12A), and in the second, third, and fourth columns (e.g., E18, E10, E2; FIG. 12B). Consider also the tripole in FIG. 12C with a horizontal focus of 1.5. Here, all four columns of electrodes are needed to form the tripole, and thus this tripole is not one that can conventionally be horizontally steered.

This is addressed by implementing a new steering algorithm in the relevant external device (e.g., 45 or 50) that is used for steering the target poles. The steering algorithm preferably automatically modifies the relative amplitude of the target poles once they are steered to an electrode array boundary. As will be shown, once a target pole is steered to an electrode array boundary, further steering in the direction of that boundary results in a gradual decrease in the relative amplitude of that target pole. Eventually, continued steering in that direction will cause that target pole to disappear. Thus, in the case of a target tripole, continued steering will eventually cause the target tripole to be automatically converted into a target bipole.

The steering algorithm, like the electrode configuration algorithm 110 (FIG. 7), can be implemented and stored as software, firmware, or microcode operable within control circuitry (e.g., 70 or 48, FIG. 4) of the relevant external device (45 or 50). Such control circuitry can comprise one or more microprocessors, microcomputers, Digital Signal Processors (DSPs), FPGAs, or other circuitry capable of executing programs in a computing device. In one example, the control circuitry any of the i5 processors manufactured by Intel Corp., as described at https://www.intel.com/content/www/us/en/products/processors/core/i5-processors.html, and may include associated internal or external memory for storing the algorithms. Such control circuitry may also include instructions for rendering and receiving input from the GUI 100 (FIG. 6). The algorithms can be stored on a non-transitory computer readable media, such as a solid state, optical, or magnetic memory, and loaded into the relevant external device.

A first example of operation of the steering algorithm is shown in FIGS. 13A-13D. FIG. 13A starts with the horizontal target tripole illustrated at the bottom of FIG. 12C, which has a focus of 1.5, with anode target poles at the electrode array boundaries (e.g., E26 and E2), and with a cathode target pole between them (e.g., between E18 and E10). Even though the target tripole is currently established with target poles at the left and right boundaries at the electrode array (i.e., at E26 and E2), the target tripole can still be horizontally steered using the steering option 112 of GUI 100 (FIG. 6). As noted above, such steering 112 allows the target poles to be steered by any amounts, and not necessarily at discrete physical electrode increments.

In FIG. 13B these initial target poles are steered 0.5 to the left, which moves all active electrodes 0.5 to the left if possible. Thus, the cathode C (previously between E18 and E10) moves to E18 (100%*−I), and anode A2 (previously at E2) moves between electrodes E10 and E2. Again, electrode configuration algorithm 110 will operate to select active electrodes, polarities, and relative amplitudes to best approximate the electric field in the tissue warranted by the new target pole positions. For example, cathode target pole's C position can now be established wholly at electrode E18 (100%*−I) as shown. By contrast, anode target pole A2 would now likely be established by the algorithm 110 by providing some portion of the anode current +I to electrodes E10 and E2.

Anode target pole A1 was initially established at the left boundary of the electrode array (E26), and thus cannot move 0.5 to the left. However, its relative amplitude can be automatically be decreased by the steering algorithm in lieu of being moved. This still allows the target tripole to be effectively steered to the left, despite having "hit" the boundary of the electrode array 17 or 17'. This is beneficial, as it still allows the basic configuration of the target poles (e.g., the tripole) to be moved, even though the configuration is modified. As such, additional flexibility is provided to recruit neural fibers to the left of the original tripole, despite hitting the boundary.

The relative amplitude of a target pole at the boundary, if steering continues in that direction, can be automatically decreased by the steering algorithm in different manners, depending on how the steering algorithm in the external device is programmed. In one example not shown in FIG. 13B, the relative amplitude of anode target pole A1 can be automatically decreased by a set amount, such as by reducing it to 80% of its original value. Using this scheme, anode target pole A1 would now have a relative amplitude 50%*80%*+I, or 40%*+I. This then affects the relative amplitude of the other anode target pole A2, which must receive the remainder of the total anodic current, or 60%*+I. Because anode target pole A2 in FIG. 13B is not located at the position of a physical electrode, electrode configuration algorithm 110 would select surrounding electrodes as necessary. For example, the algorithm 110 might establish the 60% anodic current A2 requires by selecting and providing 30%*+I to each of electrode E10 and E2.

Preferably, the relative amplitude of target pole A1 is automatically reduced using a mathematical formula, which may consider the relative positions of the target poles. In another example not shown in FIG. 13B, the distance between the anode target poles and the cathode target pole can be considered and used to weight the relative amplitude at A1. For example, the distance between A1 and C is 1.0, while the distance between A2 and C is 1.5, for a total distance of 2.5. As such, the relative amplitudes of A1 and A2 can be weighted based upon these distances relative to the total distance. For example, A1 can be weighted to receive 1/2.5, or 40% of the anodic current (40%*+I), while A2 can receive 1.5/2.5, or 60% of the anodic current (60%*+I). Again, this anodic current would be split at electrodes E10 and E2, or 30% a piece.

In another alternative shown in FIG. 13B, the relative amplitude of A1 can be automatically reduced by considering the desired focus of the target poles and the maximum amount that the target poles can be steered in the relevant direction. In this regard, the target poles' center, for example the cathode C (CPS), is allowed in the disclosed technique to be steered all the way to the boundary of the electrode array 17 or 17'. This means that the initial tripole shown in FIG. 13A can be steered 1.5 columns to the left (with the cathode C moving to E26) and 1.5 columns to the right (with cathode C moving to E2). Note that these maximum steering distances can be computed by the steering algorithm given the layout of the electrode array 17 or 17', and can be displayed in GUI 100 at indicators 122 and 124 respectively, which assists the clinician or patient in understanding how far they can steer the target poles (112) in these directions. Similarly, indicators 126 and 128 respectively show how far the target poles can be steered up or down. Note that the steering algorithm can automatically calculate and update the maximum steering distance indicators 122-128 because it knows both the current position of the target poles, and the electrode array boundaries by virtue of the selected electrode lead(s) representations 102 chosen (FIG. 6).

When the initial tripole is steered 0.5 to the left in FIG. 13B, the maximum left steering distance 122 is now decreased to 1.0, showing that the tripole can only be steered this much further to the left. In other words, there is 1.0 between anode target poles A1 and C. The maximum right steering distance 124 is increased to 2.0. The relative amplitude of anode target pole A1 at the boundary can then be adjusted by reducing it by a ratio of the relevant (left) remaining maximum steering distance (1.0, or the distance between C and A1) and the otherwise set focus of the target poles (1.5), or a ratio of 66.6%. Thus, A1 may be adjusted from its initial value to 50%*66.7%*+I by this ratio, or to 33.3%*+I. Anode target pole A2 will then receive the remaining anodic current, or 66.7%*+I, which again would likely be split by the electrode configuration algorithm 110 between electrodes E10 and E2 as already explained.

If the tripole is moved another 0.5 to the left, FIG. 13C results. As before, target poles that can move another 0.5 increment are moved: anode target pole A2 is moved to E10, and cathode target pole C is moved to between E26 and E18. Anode target pole A1's relative amplitude is then further reduced by the steering algorithm, using for example the manners previously mentioned. It can be reduced by another set amount, such as to 60% of its original value (60%*50%*+I, or 30%*+I), with the remaining 70%*+I being provided to the other anode target pole A2. A1's relative amplitude can also be reduced based on the relative positions of the target poles: the distance between A1 and C is 0.5, while the distance between A2 and C is 1.5, for a total distance of 2.0, such that A1 can receive 0.5/2.0, or 25% of the anodic current (25%*+I), while A2 receives the remainder (75%*+I). Or, as illustrated in FIG. 13C, A1's relative amplitude can reduced by considering the desired horizontal focus of the target poles (1.5) and the maximum amount that the target poles can be steered in the relevant direction (0.5). This establishes a ratio of 0.5/1.5 or one-third, which when applied to A1's initial relative amplitude (50%*+I) renders a relative amplitude of 50%*33.3%*+I, or 16.7%*+I. A2 would receive the remainder of 83.3%*+I for proper charge balancing. Note that the maximum left and right steering distances 122 and 124 are updated by the steering algorithm to 0.5 and 2.5 respectively.

If steered another 0.5 increment to the left, as shown in FIG. 13D, the cathode C is now located at the boundary of the electrode array, i.e., at E26, and A2 is now established between electrodes E18 and E10. At this point, the steered target tripole has now become a target bipole: A1 is no longer active, and cathode C and anode A2 receive the entirety of the cathodic current −I and anodic current +I respectively. Note that the maximum left steering distance 122 is now set to zero, meaning that the target poles cannot in this example be steered any further in that direction.

FIG. 14 shows another example of a paddle lead 19' to show applicability of the disclosed steering algorithm even if the electrodes 16 in the array 17 or 17' are not arrayed in strict columns and rows. In this example, notice that columns 1 and 4 of the electrodes are offset relative to columns 2 and 3, and so the electrodes are not formed in a perfect grid pattern. However, this doesn't matter, and in fact the electrodes in the array can appear at random locations, because the electrode configuration algorithm 110 can operate as before to establish the target poles at any desired locations. FIGS. 15A-15D thus show the same horizontal steering of the target tripole as was illustrated in FIGS. 13A-13D. The only difference here is that the electrode configuration algorithm 110 would modify the selected electrodes, polarities, and relative amplitudes as necessary given the different locations of the physical electrodes.

To this point, the disclosed steering algorithm has been illustrated with respect to a paddle lead 19 or 19', which provides an array 17 or 17' of physical electrodes 16 in both horizontal and vertical directions. However, the technique is not so limited, and may be used with other types of electrode arrays as well. For example, FIGS. 16A-16D show application of the steering technique as applied to a 1×8 electrode array as provided by a single percutaneous lead 15 (FIG. 1). A target tripole has been established vertically at electrodes E2 (A1), E4 (C), and E6 (A2). The vertical focus 120 (FIG. 6) of these target poles is thus 2.0, and the tripole can still be steered upward a maximum distance of 3.0 (126) in accordance with the steering algorithm. This tripole is steered vertically upwards (112, FIG. 6) in increments of 1.0 in this example, and so in FIG. 16B, the tripole simply shifts upwards to electrodes E1 (A1), E3 (C), and E5 (A2), with the tripole still able to be steered upward another 2.0 (126).

However, anode target pole A1 in FIG. 16B is now at a boundary of the electrode array (E1). Thus, if the target poles are steered another 1.0 upwards, as shown in FIG. 16C, C and A2 move by the designated amount (to E2 and E4 respectively), but anode target pole A1's relative amplitude is diminished. Again, this reduction in relative amplitude can occur in different manners, but using an example described above, the relative amplitude of A1 can be reduced considering the desired vertical focus of the target poles (120; 2.0) and the maximum amount that the target poles can still be steered in the relevant direction (126; 1.0) in accordance with the disclosed technique. This establishes a ratio of 50%, and so in FIG. 16C, target pole A1's initial relative amplitude is reduced by 50% to 50%*50%*+I, or 25%*+I. Anode target pole A2 thus receives the remaining 75%*+I of total anodic current. If the target poles are moved another 1.0 upward, and cathode target pole is at the boundary of E1, and the target poles cannot be steered farther upwards. Anode target pole A1 previously at the boundary has disappeared, at anode target pole A2, now at E3, receives 100%*+I.

It should be noted that the steering algorithm is reversible to reestablish the target tripole should the target poles be moved away from the relevant boundary. For example, if the target poles are steered downward starting from FIG. 16D, the target pole configurations of FIGS. 16C, 16B, and 16A will result in sequence. Likewise if the target poles are steered to the right in FIG. 13D, the target pole configurations of FIGS. 13C, 13B, and 13A will result in sequence, etc.

Figure 17:
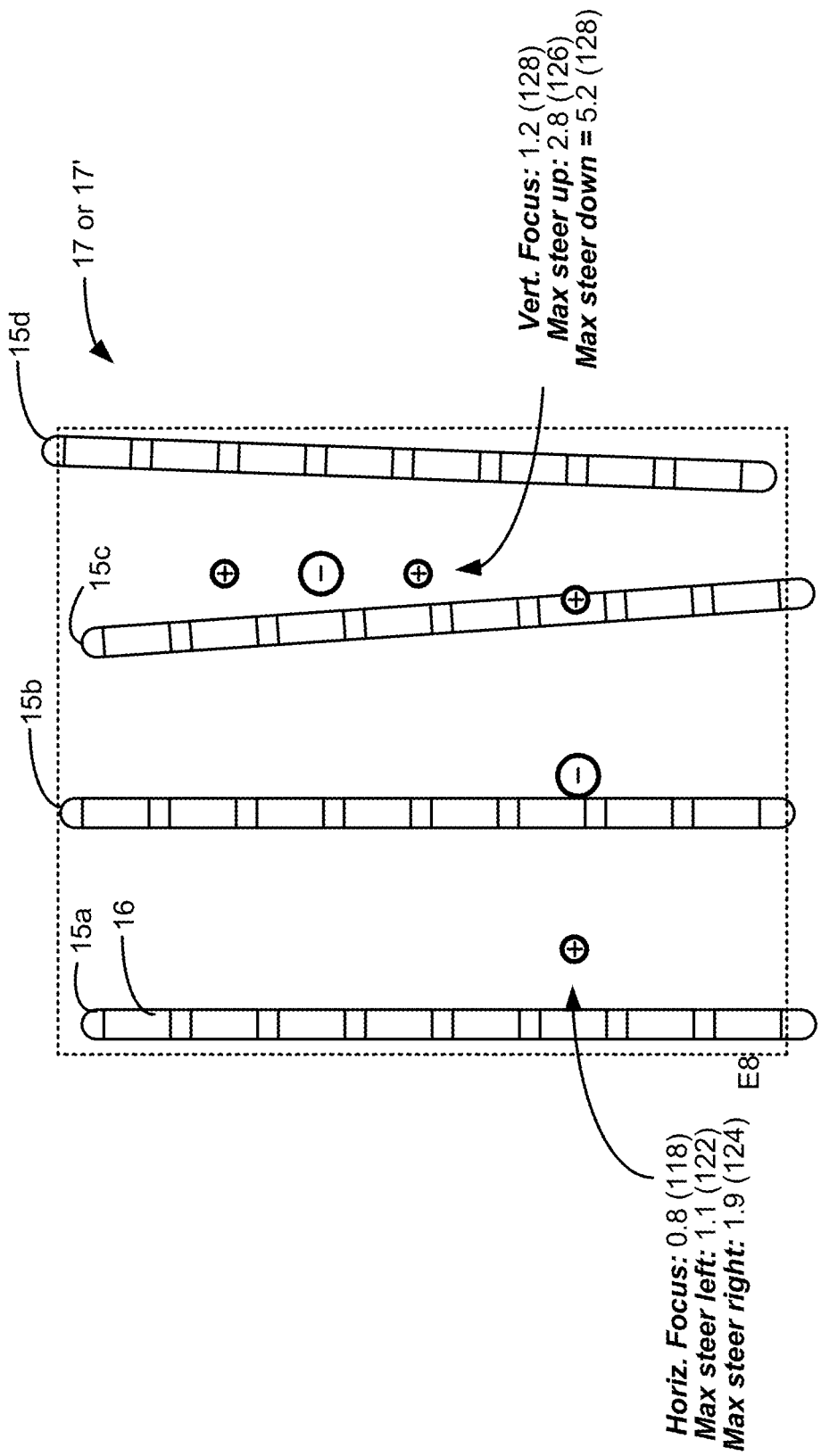
FIG. 17 shows target pole definition and operation of the steering algorithm using multiple percutaneous leads.

FIG. 17 shows applicability of the disclosed steering algorithm to an array 17 or 17' formed by a plurality of electrode leads. Four such percutaneous leads 15a-d are shown, but more or fewer could be used. Example vertical and horizontal target pole configurations are shown which can be established by the electrode configuration algorithm 110 (FIG. 7) using electrodes on one or more of leads 15a-15d. Note that the electrodes on leads 15a-15d are not lined up in a perfect grid, which may not be surprising as this can be difficult to establish when the leads are implanted in the patient. Nonetheless, the positions of the electrodes 16 after implantation can generally be assumed. The positions of the electrodes 16 can also be known, such as with the assistance of the fluoroscopic image 101 provided by GUI 100 described earlier (FIG. 6), with such known positions being available to the electrode configuration algorithm 110 and the steering algorithm operable in the external device (e.g., 45 or 50). Further, the assumed or known positions of the electrodes can be used by the steering algorithm to determine the boundary—shown in dotted lines—of the electrode array, and therefore which electrodes are at the boundary. Thus, the vertical and horizontal target poles can be steered as described earlier, i.e., by reducing the relative amplitude of target poles at the boundary as described.

Figure 18:
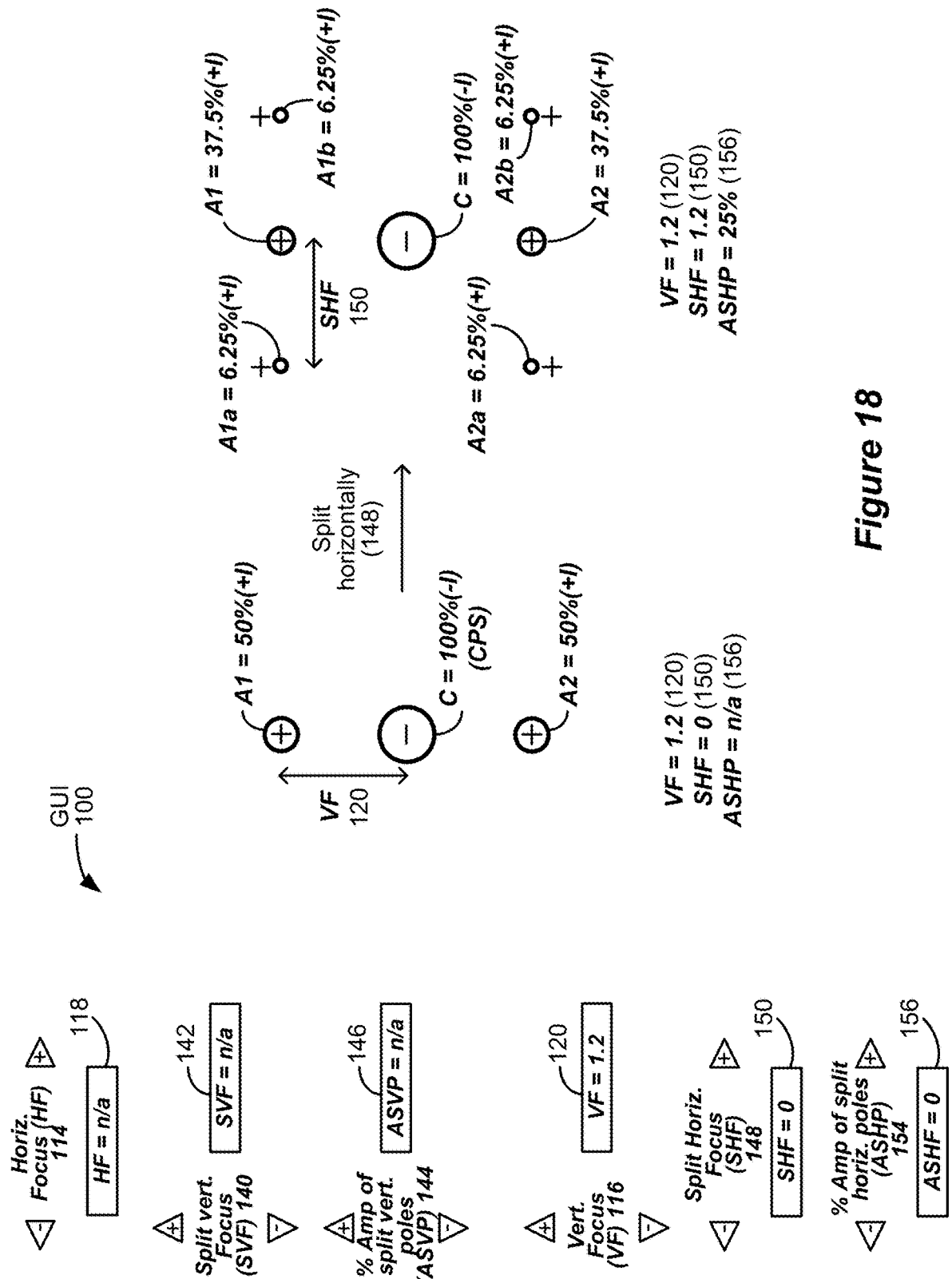
FIG. 18 shows a modified GUI having means to steer current by splitting target poles in a direction orthogonal to target pole definition.

FIG. 18 illustrates another useful manner in which target poles can be steered, and provides additional controls in GUI 100 to facilitate such steering. In this example, target poles defined linearly in one direction can be split in an orthogonal direction to create target poles that are two dimensional.

For example, FIG. 18 shows an initial target tripole configuration which is defined along a vertical axis. As before, the target poles are defined by their location, polarities, and relative amplitudes, with C=100%*−I and A1=A2=50%*+I. However, target poles other than the central pole, i.e., the anode target poles in the illustrated example, are split left and right of the vertical axis in the horizontal direction, thus creating new anode target poles A1a and A1b to the left and right of anode target pole A1, and split anode target poles A2a and A2b to the left and right of anode target pole A2. This allows nerve fibers in the transverse direction of the initial target poles to be recruited, and so improves the coverage of stimulation. Once the target poles have been split, and as before, electrode configuration algorithm 110 can operate to select physical electrodes, polarities, and relative amplitudes to best approximate the positions, polarities, and relative amplitudes of the target poles.

FIG. 18 shows additional user interface aspects in GUI 100 that can be used to prescribe how the target poles can be split. A split horizontal focus option 148 is provided to allow the user to set a split horizontal focus distance (SHF) at which the new split horizontal target poles will be formed relative to the original anode target poles; this distance SHF can also be indicated at 150. (If the target poles are not split, as in the initial configuration, SHF would be set (148) to 0). In the example shown, the split horizontal focus SHF equals the vertical focus VF of the initial target poles (1.2), but this isn't required, as these distances can be set to different values at options 148 and 116 respectively.

Figure 19:
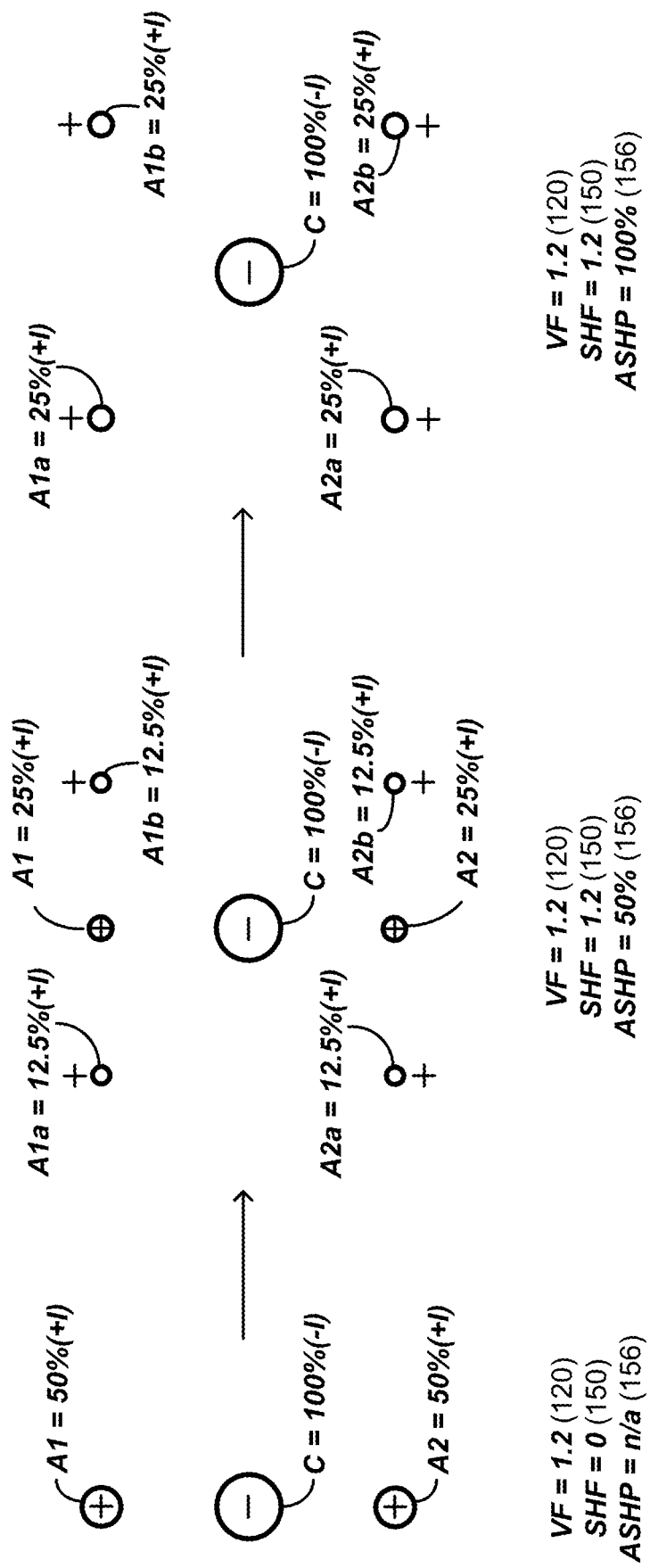
FIG. 19 shows horizontal splitting of vertically-aligned target poles.

Further, the percentage of the current that is steered from the initial target poles to the split horizontal target poles is also controllable in GUI 100 using option 154. Option 154 allows the relative amplitude of the split horizontal target poles to be set as a percentage of the relative amplitude of the initial target poles (ASHP), which percentage can be indicated at 156. In the example of FIG. 19, ASHP 156 is set to 25%. This means that 25% percent of anode target pole A1 (25%*50%*+I, or 12.5%*+I) will be moved to and shared between split anode target poles A1a and A1b, with each receiving 6.25%*+I. This leaves 37.5%*+I at the original anode target pole A1. The same splitting of current results between A2 and A2a and A2b, with each receiving 37.5%, 6.25% and 6.25% of +I respectively.

FIG. 19 shows in sequence the effect of steering current to the split horizontal target poles. The vertical target tripole at the left is as described earlier, and hasn't yet been horizontally split. Thus, SHF equals 0, and since there are no split horizontal target poles, their relative amplitude, ASHP, is irrelevant ("n/a").

In the middle of FIG. 19, some definition of the split horizontal target poles A1a, A1b, A2a, and A2b has occurred. Using option 148, they are positioned from their original target poles with a split horizontal focus (SHF) of 1.2 (150), and using option 154, they are provided 50% of their original target poles' relative amplitude; in other words, ASHP equals 50%. Thus, split horizontal target poles A1a and A1b in total receive 50% of target pole A1's relative amplitude, or 25%*+I, which is shared between each (12.5%*+I). Split horizontal target poles A2a and A2b likewise receive 50% of target pole A2's relative amplitude, each receiving 12.5%*+I. Original target poles A1 and A2 each receive the remaining 25% of +I.

At the right of FIG. 19, ASHP has been adjusted (148) to 100%, meaning that the split horizontal target poles now receive all of their associated target pole's current; as such, initial target poles A1 and A2 have an amplitude of 0, and are thus no longer present. Split horizontal target poles A1a and A1b in total receive all of target pole A1's relative amplitude, or 50%*+I, which is shared between each (25%*+I). Split horizontal target poles A2a and A2b likewise receive all of target pole A1's relative amplitude, or 25%*+I each.

Figure 20:
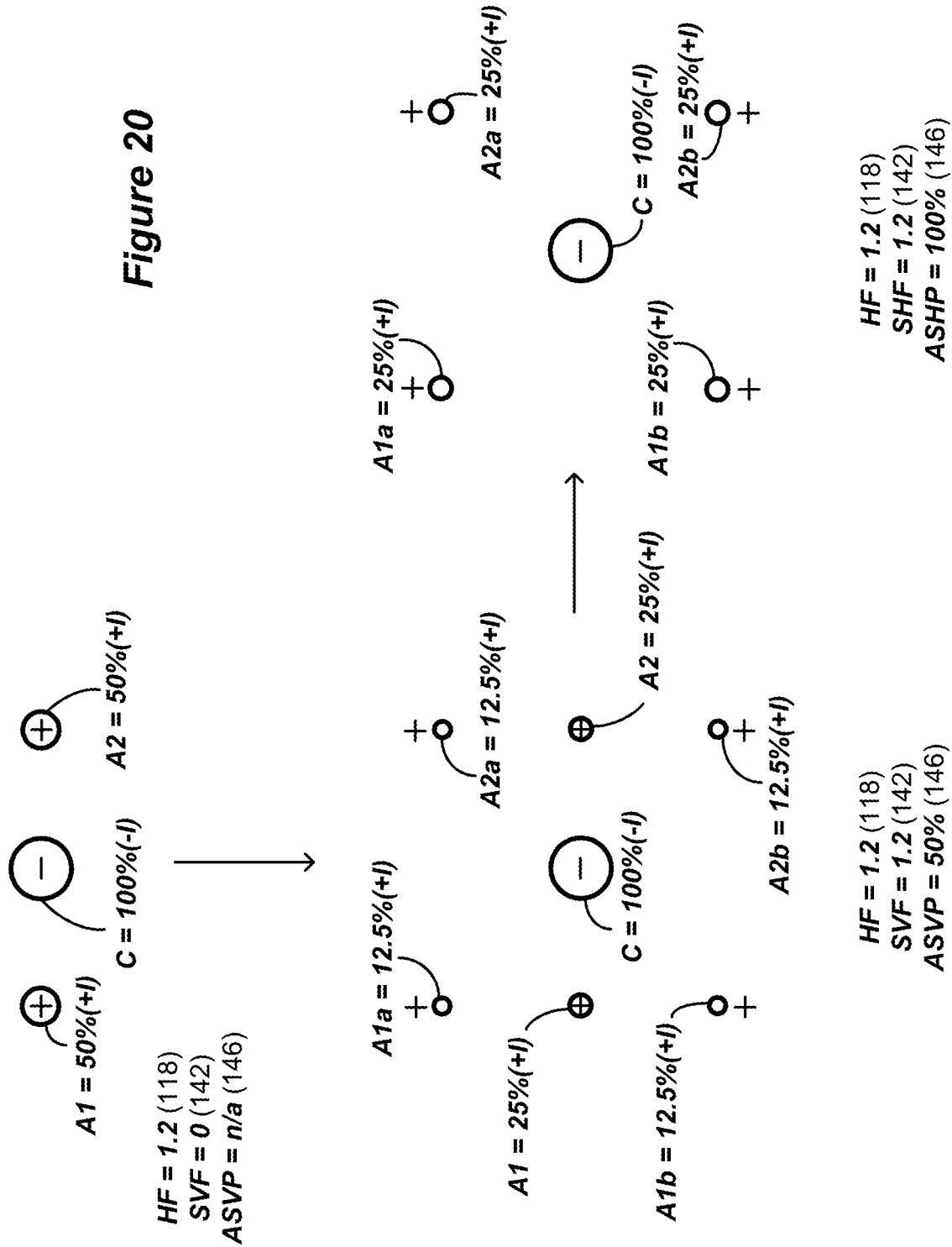
FIG. 20 shows vertical splitting of horizontally-aligned target poles.

Referring again to the GUI 100 of FIG. 18, note that analogous options and indicators are provided for the steering and splitting of horizontal target poles, including options 140 and 144 to set a split vertical focus distance (SVF) and a percentage amplitude of such split vertical target poles (ASVP), including indicators 142 and 146 to show their current values. Splitting of a horizontal tripole is shown in FIG. 20 in sequential steps, analogous to what occurred in FIG. 19, and so this figure should be self-explanatory.

Figure 21:
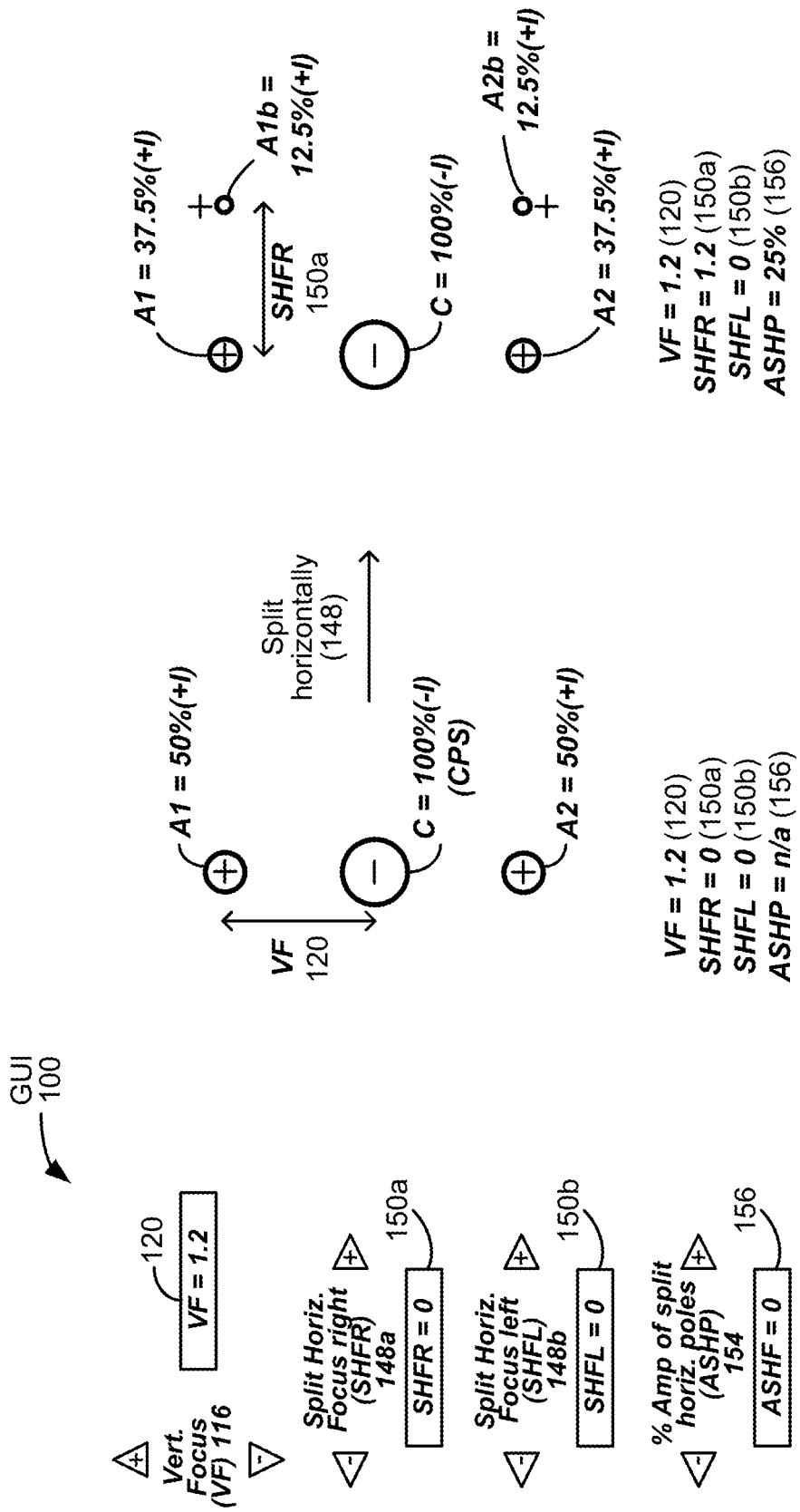
FIG. 21 shows splitting of target poles to only one side of the poles' axis.

FIG. 21 shows an alternative in which anode target poles A1 and A2 are each split to respectively form a single horizontal split target pole A1b and A2b to only one side of the vertical axis of the target tripole. In this example, the split poles A1b and A2b are formed to the right of the axis, and in this regard the GUI 100 can be modified to allow a split horizontal focus to be set (148a) to the right of the axis (SHFR 150a), and to allow a split horizontal focus to be set (148b) to the left of the axis (SHFR 150b). Thus, after splitting and as shown to the right in FIG. 21, SHFR is set to 1.2 (150a), while SHFL is set to zero (150b), meaning that the split target poles will only appear to the right of the axis of the original target tripole. Furthermore, the relative amplitude of the split horizontal poles ASHP (156) is set to 25%. Because each original target pole A1 and A2 is only horizontally split into one other poles A1b and A2b, these poles will each receive 25% of the original target poles' relative amplitude, or 50%*25%*+I or 12.5%*+I a piece. Original target poles A1 and A2 will thus receive the remaining 37.5%*+I a piece. Although not shown, note that GUI 100 can also contain options akin to 150a and 150b to split an original horizontal tripole (e.g., FIG. 20) only up or down.

Figure 22:
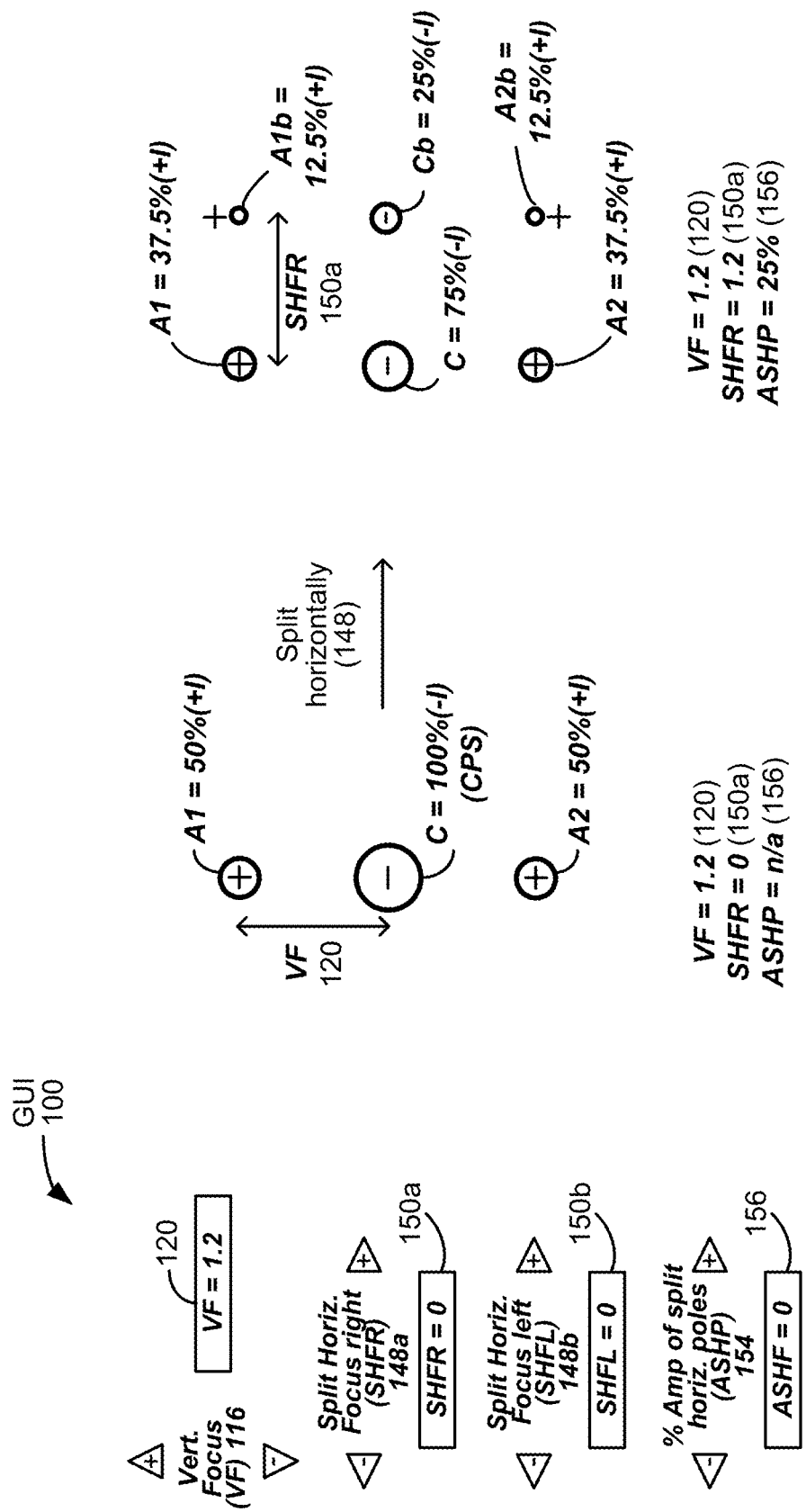
FIG. 22 shows splitting of all target poles, including the central pole.

FIG. 22 shows yet another option in which the central target pole, e.g., cathode target pole C, is also split along with the anode target poles A1 and A2. This example is akin to FIG. 21 in that it only shows right-side splitting of the poles, but splitting of all original target poles to both sides of the vertical axis can also occur as shown in FIG. 18, although this isn't illustrated for simplicity. Note in FIG. 22 that by setting SHFR to 1.2 the anode target poles A1 and A2 are split forming new anode target poles A1b and A2b on the right. Additionally, the central target pole C is also split to the right by the same distance (SHFR), forming pole Cb. In accordance with the set relative amplitude of the split horizontal poles (ASHP 156), Cb will be formed with 25% of original target pole C's value, or 25*−I, leaving the remaining cathodic current to cathode target pole C, or 75%*−I.

It should be noted that splitting of the target poles as illustrated is not limited to the example shown in which a target tripole is split. The target poles could comprise more than four target poles, or even two target poles (i.e., a target bipole), although this isn't illustrated. In a target bipole defined along an axis for example, both poles or only one could be split orthogonally to the axis (like in FIG. 22), and such splitting can result in each split pole comprising only a pair of split poles on both sides of the axis, or only one split pole on a single side of the axis.

Again, it should be noted that electrode configuration algorithm 110 (FIG. 7) can operate if necessary to form the electrode configurations necessary to realize the target poles in any of FIGS. 18-22. Further, the various manners of splitting target poles shown in FIGS. 18-22 can be used in any combination, even if such alternative combinations aren't shown.

While this disclosure has used terms like directional terms such as up, down, left, right, vertical, and horizontal in describing the position or movement of target poles, it should be understood that these terms are merely relative to the figures as they have been drawn, and should not be construed in a literal sense.

It should be noted that while the disclosed electrode configuration algorithm 110 (FIG. 7) can be useful in defining an electrode configuration that approximates the formation of the target poles, use of an electrode configuration algorithm is not always necessary. This is particularly true if the target poles are located exclusively at the location of physical electrodes in an electrode array 17 or 17', and if these target poles are likewise only steered to such physical electrodes (e.g., FIGS. 16A-16D). In such a case, the target pole and electrode configurations would be one and the same, and thus use of electrode configuration algorithm 110 would not be necessary.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
    an external device external to an implantable stimulator device comprising a graphical user interface (GUI) for programming the implantable stimulator device, wherein the implantable stimulator device comprises a plurality of electrodes configured to contact a patient's tissue, the plurality of electrodes comprising an electrode array,
    wherein the external device comprises controller circuitry programmed to execute a steering algorithm, and
    wherein the steering algorithm is configured to:
        define, via the GUI of the external device, a plurality of target poles in the electrode array, wherein the plurality of target poles are formed by providing stimulation at one or more of the electrodes; and
        receive, via the GUI of the external device, a sequence of inputs to steer the plurality of target poles within the electrode array by changing the one or more electrodes that provide the stimulation;
        wherein if one of the inputs steers the target poles in a direction toward a boundary of the electrode array such that a first of the target poles arrives at the boundary, and wherein if a next of the inputs in the sequence steers the target poles a distance amount further in the direction,
            keep the first target pole at the boundary and automatically reduce an amplitude of the first target pole, and
            steer all other of the target poles different from the first target pole by the distance amount in the direction.

2. The system of claim 1, wherein the plurality of target poles comprise a target pole configuration in which each target pole is defined by a position within the electrode array, a polarity, and a current amplitude.

3. The system of claim 2, wherein the GUI is configured to receive an input associated with a total anodic and cathodic current amplitude to be shared between the target poles.

4. The system of claim 2, wherein the controller circuitry is further programmed with and configured to execute an electrode configuration algorithm, wherein the electrode configuration algorithm is configured to automatically determine, from the target pole configuration, active electrodes, polarities of the active electrodes, and current amplitudes of the active electrodes that provide the stimulation at the one or more of the plurality of electrodes.

5. The system of claim 1, wherein one of the other target poles comprises a central target pole.

6. The system of claim 5, wherein the target poles have a focus distance in the direction relative to the central target pole, and wherein the steering algorithm is further configured to:
    if the next of the inputs in the sequence steers the target poles the distance amount further in the direction, automatically reduce the amplitude of the first target pole based on a first distance between the first target pole and the central target pole and the focus distance.

7. The system of claim 1, wherein the plurality of target poles comprises a tripole, wherein the first target pole comprises an anode, a second of the other target poles comprises a cathode, and a third of the other target poles comprises an anode, and wherein the steering algorithm is further configured to:
    if the next of the inputs in the sequence steers the target poles the distance amount further in the direction, automatically reduce an amplitude of the first target pole by a first value and automatically increase an amplitude of the third target pole by a second value.

8. The system of claim 1, wherein the first value and the second value are equal.

9. The system of claim 1, wherein the steering algorithm is further configured to:
    if the next of the inputs in the sequence steers the target poles the distance amount further in the direction, remove the first target pole or set an amplitude of the first target pole to zero.

10. The system of claim 9, wherein the plurality of target poles comprises a tripole, and wherein the steering algorithm is further configured to:
    if the next of the inputs in the sequence steers the target poles the distance amount further in the direction, modify the target poles from the tripole to a bipole.

11. The system of claim 1, further comprising the implantable stimulator device.

12. The system of claim 11, wherein the implantable stimulator device comprises a fully-implantable implantable pulse generator.

13. The system of claim 11, wherein the implantable stimulator device comprises an external trial stimulator coupled to the electrode array, wherein the electrode array is implantable in a patient.

14. The system of claim 1, wherein the electrode array comprises a horizontal dimension that is smaller than a vertical dimension.

15. The system of claim 14, wherein the target poles comprise a horizontal target pole configuration.

16. The system of claim 1, wherein the electrode array comprises a paddle lead.

17. The system of claim 1, wherein the electrode array comprises one or more percutaneous leads.

18. A non-transitory computer readable medium comprising instructions executable on an external device external to an implantable stimulator device comprising a graphical user interface (GUI) for programming the implantable stimulator device, wherein the implantable stimulator device comprises a plurality of electrodes configured to contact a patient's tissue, the plurality of electrodes comprising an electrode array, wherein the instructions comprise a steering algorithm, wherein the steering algorithm when executed is configured to:
    define, via the GUI of the external device, a plurality of target poles in the electrode array, wherein the plurality of target poles are formed by providing stimulation at one or more of the electrodes; and receive, via the GUI of the external device, a sequence of inputs to steer the plurality of target poles within the electrode array by changing the one or more electrodes that provide the stimulation;

wherein if one of the inputs steers the target poles in a direction toward a boundary of the electrode array such that a first of the target poles arrives at the boundary, and wherein if a next of the inputs in the sequence steers the target poles a distance amount further in the direction, keep the first target pole at the boundary and automatically reduce an amplitude of the first target pole, and steer all other of the target poles different from the first target pole by the distance amount in the direction.

* * * * *